United States Patent
Levy et al.

(10) Patent No.: US 11,408,036 B2
(45) Date of Patent: Aug. 9, 2022

(54) METHODS OF ASSESSING AND MONITORING TUMOR LOAD

(71) Applicant: Lexent Bio, Inc., San Francisco, CA (US)

(72) Inventors: Samuel Levy, La Jolla, CA (US); John C. Spinosa, La Jolla, CA (US)

(73) Assignee: Lexent Bio, Inc., Cambridge, MA (US)

( * ) Notice: Subject to any disclaimer, the term of this patent is extended or adjusted under 35 U.S.C. 154(b) by 808 days.

(21) Appl. No.: 16/173,972

(22) Filed: Oct. 29, 2018

(65) Prior Publication Data

US 2019/0300962 A1    Oct. 3, 2019

Related U.S. Application Data

(63) Continuation of application No. PCT/US2017/030231, filed on Apr. 28, 2017.

(60) Provisional application No. 62/377,446, filed on Aug. 19, 2016, provisional application No. 62/376,900, filed on Aug. 18, 2016, provisional application No. 62/328,958, filed on Apr. 28, 2016.

(51) Int. Cl.
| | | |
|---|---|---|
| *C12Q 1/6886* | (2018.01) | |
| *G16B 30/00* | (2019.01) | |
| *G16B 20/00* | (2019.01) | |
| *C12Q 1/6806* | (2018.01) | |
| *C12Q 1/68* | (2018.01) | |
| *G16B 20/20* | (2019.01) | |
| *G16B 30/10* | (2019.01) | |
| *G16B 20/10* | (2019.01) | |

(52) U.S. Cl.
CPC ............ *C12Q 1/6886* (2013.01); *C12Q 1/68* (2013.01); *C12Q 1/6806* (2013.01); *G16B 20/00* (2019.02); *G16B 20/10* (2019.02); *G16B 20/20* (2019.02); *G16B 30/00* (2019.02); *G16B 30/10* (2019.02)

(58) Field of Classification Search
CPC ...... C12Q 1/6886; C12Q 1/68; C12Q 1/6806; G16B 30/10; G16B 20/20; G16B 20/10; G16B 30/00
See application file for complete search history.

(56) References Cited

FOREIGN PATENT DOCUMENTS

| WO | WO-2010112316 A1 | 10/2010 |
| WO | WO-2015089333 A1 | 6/2015 |
| WO | WO-2016028316 A1 | 2/2016 |
| WO | WO-2016054255 A1 | 4/2016 |
| WO | WO-2017190067 A1 | 11/2017 |

OTHER PUBLICATIONS

Bao, et al. Repbase Update, a database of repetitive elements in eukaryotic genomes. Mob DNA. 2015; 6: 11.Published online Jun. 2, 2015.doi: 10.1186/s13100-015-0041-9.
Elshimali, et al. The clinical utilization of circulating cell free DNA (CCFDNA) in blood of cancer patients. Int J Mol Sci. Sep. 13, 2013;14(9):18925-58. doi: 10.3390/ijms140918925.
Gualtieri, et al. Increased expression and copy number amplification of LINE-1 and SINE B1 retrotransposable elements in murine mammary carcinoma progression. Oncotarget. Nov. 2013; 4(11): 1882-1893. Published online: Aug. 9, 2013. DOI: 10.18632/oncotarget.1188.
Hommelsheim, et al. PCR amplification of repetitive DNA: a limitation to genome editing technologies and many other applications. Scientific Reports (4):5052 (2014). Published online: May 23, 2014. doi: 10.1038/srep05052.
Massachusetts General Hospital—Orthopaedics. Overexpression of repetitive DNA sequences discovered in common tumor cells. Web news release. Jan. 13, 2011. 2 pages. URL:<http://www.massgeneral.org/ortho/news/pressrelease.aspx?id=1327>.
Nicolaides, et al. Prenatal detection of fetal triploidy from cell-free DNA testing in maternal blood. Fetal Diagn Ther. 2014;35(3):212-7. doi: 10.1159/000355655. Epub Oct. 10, 2013.
PCT/US17/30231 International Search Report and Written Opinion dated Aug. 7, 2017.
Ribeiro, et al. Repetitive DNA alterations in human skin cancers. J Dermatol Sci. Nov. 2004;36(2):79-86.

*Primary Examiner* — Jerry Lin
(74) *Attorney, Agent, or Firm* — Morrison & Foerster LLP

(57) ABSTRACT

The invention disclosed herein generally relates to methods of assessing and monitoring tumor load through analysis of tumor DNA in cancer patients. Quantitative measures derived from cell-free DNA and germline DNA are used to assess and monitor tumor load. By assessing and monitoring tumor load, cancer may be detected in a subject. The tumor load of a subject may be assessed at a number of different time points to monitor a progression, regression, or recurrence of cancer in a subject.

29 Claims, 7 Drawing Sheets

Streck Tube

EDTA Tube

METHODS OF ASSESSING AND MONITORING TUMOR LOAD

CROSS-REFERENCE

This application claims priority to U.S. Provisional Patent Application No. 62/328,958, filed Apr. 28, 2016, U.S. Provisional Patent Application No. 62/376,900, filed Aug. 18, 2016, and U.S. Provisional Patent Application No. 62/377,446, filed Aug. 19, 2016, each of which is entirely incorporated herein by reference.

BACKGROUND

During the course of cancer treatment, tumor load may vary based on the effectiveness of the treatment. Assessment and monitoring of tumor load through non-invasive lab-based tests, such as cell-free DNA assays, may improve clinical care of cancer.

SUMMARY

Methods and systems are provided for assessing and monitoring tumor load for a subject, such as a patient with cancer. Tumor load may be assessed and monitored by analyzing tumor DNA (e.g., from cell-free DNA) from a sample of a subject in a plurality of discrete genomic windows comprising genomic regions, and generating a tumor load score based on the analysis of the tumor DNA. A tumor load score may be indicative of a tumor load in a subject. In some embodiments, a tumor load score may vary (e.g., increase or decrease) over a duration of time (e.g., over two or more different time points). In some embodiments, this duration of time may correspond to, e.g., a course of treatment for the cancer of the subject or a monitoring period after surgical resection or other treatment of a tumor (e.g., to detect recurrence of the tumor in the subject). In some embodiments, generation of a tumor load score may comprise generating a quantitative measure of cfDNA sequencing reads and/or germline DNA sequencing reads for each of a plurality of discrete genomic windows. The plurality of discrete genomic windows may comprise non-overlapping windows of a reference genome. Such non-overlapping windows may comprise non-overlapping repetitive element windows, e.g., Short Interspersed Elements (SINEs), Long Interspersed Elements (LINEs), or low copy repeats. The quantitative measure of sequencing reads may comprise a count of sequencing reads that align with each of the plurality of non-overlapping windows. In some embodiments, generation of a tumor load score may comprise generating a comparison (e.g., a ratio) of quantitative measures for cfDNA sequencing reads and germline DNA sequencing reads. By assessing a comparison of counts of sequencing reads across different sets of discrete genomic windows, methods provided herein may allow generation of tumor load scores indicative of tumor load, which can be useful for assessing or monitoring tumor load in a subject through a non-invasive lab test (e.g., a blood based test).

Methods and systems are also provided for using bioinformatics processes for enhanced detection of tumor DNA (e.g., cfDNA) signal against a background of germline DNA signal (e.g., noise). For example, enhanced detection of tumor DNA against a background germline DNA signal may comprise increasing the tumor DNA signal, decreasing the germline DNA signal, or a combination thereof.

In an aspect, disclosed herein is a method for assessing a tumor load for a subject, the method comprising: receiving sequencing information for cell-free DNA (cfDNA) from the subject gathered at a first time point and sequencing information for germline DNA from the subject, the sequencing information comprising first cfDNA sequencing reads and germline DNA sequencing reads; aligning the first cfDNA sequencing reads to a reference genome; aligning the germline DNA sequencing reads to the reference genome; generating a quantitative measure of the first cfDNA sequencing reads for each of a plurality of non-overlapping chromosomal windows of the reference genome to generate a first cfDNA set; generating a quantitative measure of the germline DNA sequencing reads for each of the plurality of non-overlapping chromosomal windows to generate a germline DNA set; and generating a first tumor load score based on a first set of ratio values, which first set of ratio values comprises, for each of the plurality of non-overlapping chromosomal windows, a ratio of the quantitative measure in the first cfDNA set to the quantitative measure in the germline DNA set, which first tumor load score is indicative of the tumor load for the subject.

In some embodiments, the method further comprises determining whether the first tumor load score is greater than a predetermined threshold, wherein a first tumor load score greater than the predetermined threshold indicates a presence of a cancer in the subject.

In some embodiments, the method further comprises: receiving sequencing information for cfDNA gathered at a second time point, the sequencing information from the second time point comprising second cfDNA sequencing reads; aligning the second cfDNA sequencing reads to the reference genome; generating a quantitative measure of the second cfDNA sequencing reads for each of the plurality of non-overlapping chromosomal windows to generate a second cfDNA set; and generating a second tumor load score based on a second set of ratio values, which second set of ratio values comprises, for each of the plurality of non-overlapping chromosomal windows, a ratio of the quantitative measure in the second cfDNA set to the quantitative measure in the germline DNA set. In some embodiments, the method further comprises determining a difference between the first tumor load score and the second tumor load score, which difference is indicative of a progression or regression of a tumor of the subject. In some embodiments, the method further comprises generating, by a computer processor, a plot of the first tumor load score and the second tumor load score as a function of the first time point and the second time point, which plot is indicative of the progression or regression of the tumor of the subject.

In another aspect, disclosed herein is a method for assessing a tumor load for a subject, the method comprising: receiving sequencing information for cell-free DNA (cfDNA) from the subject gathered at a first time point and sequencing information for germline DNA from the subject, the sequencing information comprising first cfDNA sequencing reads and germline DNA sequencing reads; aligning the first cfDNA sequencing reads to a reference genome; aligning the germline DNA sequencing reads to the reference genome; generating a quantitative measure of the first cfDNA sequencing reads for each of a plurality of non-overlapping repetitive element windows of the reference genome to generate a first cfDNA set; generating a quantitative measure of the germline DNA sequencing reads for each of the plurality of non-overlapping repetitive element windows to generate a germline DNA set; and generating a first tumor load score based on a first set of ratio values, which first set of ratio values comprises, for each of the plurality of non-overlapping repetitive element windows, a ratio of the quantitative measure in the first cfDNA set to the quantitative measure in the germline DNA set, which first tumor load score is indicative of the tumor load for the subject.

In some embodiments, the method further comprises determining whether the first tumor load score is greater than a predetermined threshold, wherein a first tumor load score greater than the predetermined threshold indicates a presence of a cancer in the subject.

In some embodiments, the method further comprises: receiving sequencing information for cfDNA gathered at a second time point, the sequencing information from the second time point comprising second cfDNA sequencing reads; aligning the second cfDNA sequencing reads to the reference genome; generating a quantitative measure of the second cfDNA sequencing reads for each of the plurality of non-overlapping repetitive element windows to generate a second cfDNA set; and generating a second tumor load score based on a second set of ratio values, which second set of ratio values comprises, for each of the plurality of non-overlapping repetitive element windows, a ratio of the quantitative measure in the second cfDNA set to the quantitative measure in the germline DNA set. In some embodiments, the method further comprises determining a difference between the first tumor load score and the second tumor load score, which difference is indicative of a progression or regression of a tumor of the subject. In some embodiments, the method further comprises generating, by a computer processor, a plot of the first tumor load score and the second tumor load score as a function of the first time point and the second time point, which plot is indicative of the progression or regression of the tumor of the subject.

In some embodiments, the plurality of non-overlapping repetitive element windows comprises a plurality of non-overlapping windows associated with repetitive elements selected from the group consisting of Short Interspersed Elements (SINEs), Long Interspersed Elements (LINEs), and low copy repeats. In some embodiments, the plurality of non-overlapping windows associated with repetitive elements selected from the group consisting of SINEs, LINEs, and low copy repeats comprises at least two distinct repetitive elements. In some embodiments, the plurality of non-overlapping windows associated with repetitive elements selected from the group consisting of SINEs, LINEs, and low copy repeats comprises at least three distinct repetitive elements. In some embodiments, the plurality of non-overlapping windows associated with repetitive elements selected from the group consisting of SINEs, LINEs, and low copy repeats comprises at least four distinct repetitive elements. In some embodiments, each of the plurality of non-overlapping repetitive element windows comprises a predetermined size of a number of base pairs.

In another aspect, disclosed herein is a method for assessing a tumor load for a subject, the method comprising: receiving sequencing information for cell-free DNA (cfDNA) from the subject gathered at a first time point and sequencing information for germline DNA from the subject, the sequencing information comprising first cfDNA sequencing reads and germline DNA sequencing reads; aligning the first cfDNA sequencing reads to a plurality of repetitive element windows from a database of repetitive element windows; aligning the germline DNA sequencing reads to the plurality of repetitive element windows; generating a quantitative measure of the first cfDNA sequencing reads for each of the plurality of repetitive element windows to generate a first cfDNA set; generating a quantitative measure of the germline DNA sequencing reads for each of the plurality of repetitive element windows to generate a germline DNA set; and generating a first tumor load score based on a first set of ratio values, which first set of ratio values comprises, for each of the plurality of repetitive element windows, a ratio of the quantitative measure in the first cfDNA set to the quantitative measure in the germline DNA set, which tumor load score is indicative of the tumor load for the subject.

In some embodiments, the method further comprises determining whether the first tumor load score is greater than a predetermined threshold, wherein a first tumor load score greater than the predetermined threshold indicates a presence of a cancer in the subject.

In some embodiments, the method further comprises: receiving sequencing information for cfDNA gathered at a second time point, the sequencing information from the second time point comprising second cfDNA sequencing reads; aligning the second cfDNA sequencing reads to the plurality of repetitive element windows; generating a quantitative measure of the second cfDNA sequencing reads for each of the plurality of repetitive element windows to generate a second cfDNA set; and generating a second tumor load score based on a second set of ratio values, which second set of ratio values comprises, for each of the plurality of repetitive element windows, a ratio of the quantitative measure in the second cfDNA set to the quantitative measure in the germline DNA set. In some embodiments, the method further comprises determining a difference between the first tumor load score and the second tumor load score, which difference is indicative of a progression or regression of a tumor of the subject. In some embodiments, the method further comprises generating, by a computer processor, a plot of the first tumor load score and the second tumor load score as a function of the first time point and the second time point, which plot is indicative of the progression or regression of the tumor of the subject.

In some embodiments, the database of repetitive element windows comprises a plurality of windows associated with repetitive elements selected from the group consisting of Short Interspersed Elements (SINEs), Long Interspersed Elements (LINEs), and low copy repeats. In some embodiments, the plurality of non-overlapping windows associated with repetitive elements selected from the group consisting of SINEs, LINEs, and low copy repeats comprises at least two distinct repetitive elements. In some embodiments, the plurality of non-overlapping windows associated with repetitive elements selected from the group consisting of SINEs, LINEs, and low copy repeats comprises at least three distinct repetitive elements. In some embodiments, the plurality of non-overlapping windows associated with repetitive elements selected from the group consisting of SINEs, LINEs, and low copy repeats comprises at least four distinct repetitive elements.

In some embodiments, the subject is human. In some embodiments, the germline DNA comprises buffy coat DNA. In some embodiments, the germline DNA comprises whole blood DNA. In some embodiments, the reference genome is at least a portion of a human genome.

In some embodiments, the quantitative measures of the cfDNA sequencing reads and the germline DNA sequencing reads are counts of DNA sequencing reads that are aligned with a given window.

In some embodiments, generating the first tumor load score based on the first set of ratio values comprises (i) performing a logarithm transformation of the first set of ratio values to generate a first set of log ratio values and (ii) performing a summation of the first set of log ratio values.

In some embodiments, generating the second tumor load score based on the second set of ratio values comprises (i) performing a logarithm transformation of the second set of ratio values to generate a second set of log ratio values and (ii) performing a summation of the second set of log ratio values. In some embodiments, the cfDNA sequencing reads and the germline DNA sequencing reads are aligned using a Burrows-Wheeler algorithm.

In some embodiments, receiving the sequencing information for cfDNA from the subject comprises obtaining a sample from the subject, isolating cfDNA from the sample, and sequencing the isolated cfDNA to produce the cfDNA sequencing reads. In some embodiments, receiving the sequencing information for germline DNA from the subject comprises obtaining a sample from the subject, isolating germline DNA from the sample, and sequencing the isolated germline DNA to produce the germline DNA sequencing reads. In some embodiments, receiving the sequencing information comprises subjecting cell-free nucleic acids of the subject to untargeted sequencing. In some embodiments, the untargeted sequencing comprises use of random primers. In some embodiments, the sample is a blood sample. In some embodiments, the method further comprises: generating a first library for use in the sequencing of the cfDNA. In some embodiments, the method further comprises: generating a second library for use in the sequencing of the germline DNA.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Definitions

Figure 1:
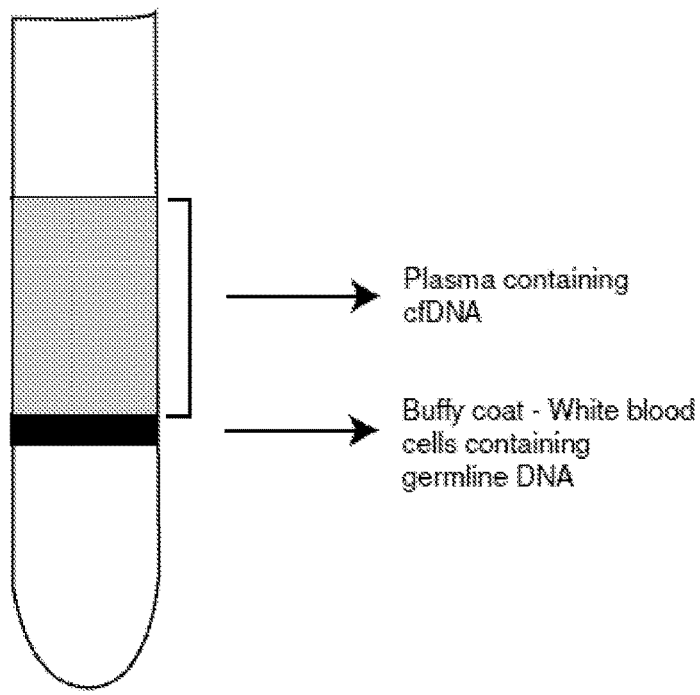
FIG. 1 illustrates an example of isolation of three types of DNA sources (plasma containing cfDNA, buffy coat containing germline DNA, and whole blood containing mostly germline DNA with some cfDNA) from a blood sample tube, in accordance with some embodiments.
Figure 1:
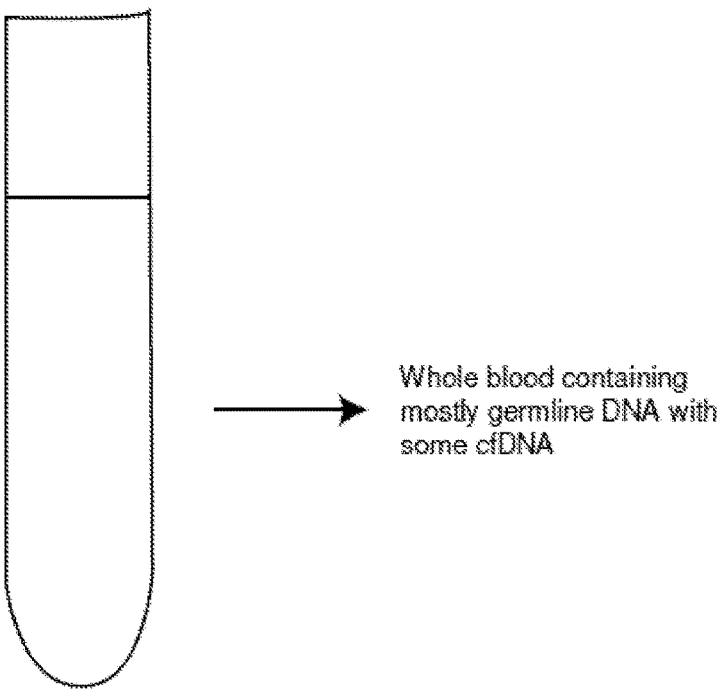

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more than 10 phosphate (P03) groups. A nucleotide can include a nucleobase, a five-carbon sugar (either ribose or deoxyribose), and one or more phosphate groups, individually or in combination.

Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. A nucleic acid molecule may be linear, curved, or circular or any combination thereof.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 5 bases, 10 bases, 20 bases, 30 bases, 40 bases, 50 bases, 60 bases, 70 bases, 80 bases, 90, 100 bases, 110 bases, 120 bases, 130 bases, 140 bases, 150 bases, 160 bases, 170 bases, 180 bases, 190 bases, 200 bases, 300 bases, 400 bases, 500 bases, 1 kilobase (kb), 2 kb, 3, kb, 4 kb, 5 kb, 10 kb, or 50 kb or it may have any number of bases between any two of the aforementioned values. An oligonucleotide is typically composed of a specific sequence of four nucleotide bases: adenine (A); cytosine (C); guanine (G); and thymine (T) (uracil (U) for thymine (T) when the polynucleotide is RNA). Thus, the terms "nucleic acid molecule," "nucleic acid sequence," "nucleic acid fragment," "oligonucleotide" and "polynucleotide" are at least in part intended to be the alphabetical representation of a polynucleotide molecule. Alternatively, the terms may be applied to the polynucleotide molecule itself. This alphabetical representation can be input into databases in a computer having a central processing unit and/or used for bioinformatics applications such as functional genomics and homology searching. Oligonucleotides may include one or more nonstandard nucleotide(s), nucleotide analog(s) and/or modified nucleotides.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules. The nucleic acid molecules may be cell-free or cell-free nucleic acid molecules, such as cell free DNA (cfDNA) or cell free RNA (cfRNA). The nucleic acid molecules may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides (e.g., cfDNA) may be fetal in origin (via fluid taken from a pregnant subject), or may be derived from tissue of the subject itself.

The term "subject," as used herein, generally refers to an individual having a biological sample that is undergoing processing or analysis. A subject can be an animal or plant. The subject can be a mammal, such as a human, dog, cat, horse, pig or rodent. The subject can be a patient, e.g., have or be suspected of having a disease, such as one or more cancers (e.g., breast cancer, colorectal cancer, brain cancer, leukemia, lung cancer, skin cancer, liver cancer, pancreatic cancer, lymphoma, esophageal cancer or cervical cancer), one or more infectious diseases, one or more genetic disorder, or one or more tumors, or any combination thereof. For subjects having or suspected of having one or more tumors, the tumors may be of one or more types. The tumors may have a tumor load (also called tumor burden) which is indicative of the total number of cancer cells in the tumors, the size of the tumors, or the total amount of cancer in the body of the subject. Each type of the one or more types of tumors may have a tumor load. A tumor load may indicate the total tumor load of all tumors (of same or different types) in the body of the subject.

The term "buffy coat," as used herein, generally refers to a fraction of a blood sample that contains most of the white blood cells and platelets following centrifugation (e.g., density gradient centrifugation) of the blood sample. The buffy coat fraction of a blood sample typically contains little or no plasma and red blood cells (erythrocytes). Buffy coat DNA (which may contain germline DNA) may be extracted from the buffy coat of a blood sample. Buffy coat DNA sequencing reads (which may contain germline DNA sequencing reads) may be extracted from buffy coat DNA.

The term "whole blood," as used herein, generally refers to a blood sample that has not been separated into sub-components (e.g., by centrifugation). The whole blood of a blood sample may contain germline DNA and/or cfDNA. Whole blood DNA (which may contain germline DNA and/or cfDNA) may be extracted from a blood sample. Whole blood DNA sequencing reads (which may contain germline DNA sequencing reads and/or cfDNA sequencing reads) may be extracted from whole blood DNA.

Since tumors typically comprise one or more DNA mutation events, such mutation events may be detectable, thereby allowing the detection and quantification of tumor DNA to be used toward generating one or more tumor load scores indicative of the tumor load of a subject.

Assessing Tumor Load by Increasing Relative Tumor DNA Signal in DNA Sequence Data from a Subject Detection of DNA mutation events may be relatively straightforward when a significant portion (e.g., >80%) of a sample taken from a subject comes from or is derived from tumor cells. However, in a cell free DNA (cfDNA) preparation from a subject's plasma derived from a blood sample, the detection of tumor DNA from the cfDNA may be an insensitive and noisy process. Detection of tumor DNA from such insensitive and/or noisy signals may be challenging due to the overwhelming signal from non-tumor DNA (e.g., from germline DNA from germline cells that are not tumor derived). Thus, there is a need to increase the tumor DNA portion of such a signal and/or to minimize the germline DNA noise. The present disclosure provides methods and systems to facilitate the detection of tumor DNA from DNA sequence data (e.g., DNA sequencing reads) derived from a sample of a subject. The DNA sequence data taken from a subject may comprise cfDNA sequencing reads, buffy coat DNA sequencing reads, and/or whole blood DNA sequencing reads. Once DNA sequence data has been received from analysis of a sample from the subject, one or more bioinformatics processes may be used to enhance tumor DNA signal against a background germline DNA noise. Enhancement of the tumor DNA signal against the background germline DNA noise may comprise increasing the tumor DNA signal, decreasing the germline DNA noise, or a combination of increasing the tumor DNA signal and decreasing the germline DNA noise.

Three examples of bioinformatics processes that may be used to increase relative tumor DNA signals are discussed below.

A. Methods for Assessing Tumor Load Using Non-Overlapping Chromosomal Windows

In an aspect, disclosed herein is a method for assessing a tumor load for a subject, the method comprising: receiving sequencing information for cell-free DNA (cfDNA) from the subject gathered at a first time point and sequencing information for germline DNA from the subject, the sequencing information comprising first cfDNA sequencing reads and germline DNA sequencing reads; aligning the first cfDNA sequencing reads to a reference genome; aligning the germline DNA sequencing reads to the reference genome; generating a quantitative measure of the first cfDNA sequencing reads for each of a plurality of non-overlapping chromosomal windows of the reference genome to generate a first cfDNA set; generating a quantitative measure of the germline DNA sequencing reads for each of the plurality of non-overlapping chromosomal windows to generate a germline DNA set; and generating a first tumor load score based on a first set of ratio values, which first set of ratio values comprises, for each of the plurality of non-overlapping chromosomal windows, a ratio of the quantitative measure in the first cfDNA set to the quantitative measure in the germline DNA set, which first tumor load score is indicative of the tumor load for the subject.

In some embodiments, generation of a tumor load score may comprise receiving sequencing information for cell-free DNA (cfDNA) from the subject gathered at a first time point from the subject, the sequencing information comprising first cfDNA sequencing reads. Any of the first, second, third, or subsequent time points may correspond to any time point during the course of diagnosis, prognosis, or treatment of a cancer in the subject (e.g., diagnosing a cancer comprising one or more tumor types in the subject, prognosing a cancer comprising one or more tumor types in the subject, before initiating a course of treatment (e.g., surgical resection, chemotherapy, radiotherapy, immunotherapy, targeted therapy) to treat the cancer in the subject, during the course of treatment, before initiating a second, third, or other subsequent course of treatment, or during the course of the second, third or other subsequent course of treatment to treat the cancer in the subject). Sequencing reads may be generated from the cfDNA using any suitable sequencing method known to one of skill in the art.

In some embodiments, generation of a tumor load score may comprise receiving sequencing information for germline DNA from the subject, the sequencing information comprising germline DNA sequencing reads. Germline DNA may comprise buffy coat DNA and/or whole blood DNA. Germline DNA sequencing reads may be comprise sequencing reads of the buffy coat DNA and/or the whole blood DNA. Germline DNA may be acquired from the same sample from which cfDNA is obtained, or may be acquired from another sample at the same time point from which cfDNA is obtained, or may be acquired from a sample different from the sample from which cfDNA is obtained at the same time point, or may be acquired from a sample different from the sample from which cfDNA is obtained at a different time point.

In some embodiments, generation of a tumor load score may comprise aligning the first cfDNA sequencing reads to a reference genome. The reference genome may comprise at least a portion of a genome (e.g., the human genome). The reference genome may comprise an entire genome (e.g., the entire human genome). The reference genome may comprise a database comprising a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and repetitive elements (LINEs, SINEs, and/or low copy repeats)). The alignment may be performed using a Burrows-Wheeler algorithm or any other alignment algorithm known to one who is skilled in the art.

In some embodiments, generation of a tumor load score may comprise aligning the germline DNA sequencing reads to a reference genome. The reference genome may comprise at least a portion of a genome (e.g., the human genome). The reference genome may comprise an entire genome (e.g., the entire human genome). The reference genome may comprise a database comprising a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and repetitive elements (LINEs, SINEs, and/or low copy repeats)). The alignment may be performed using a Burrows-Wheeler algorithm or any other alignment algorithm known to one who is skilled in the art. The cfDNA sequencing reads and the germline DNA sequencing reads may be aligned to the same reference genome or different reference genomes.

In some embodiments, generation of a tumor load score may comprise generating a quantitative measure of the first cfDNA sequencing reads for each of a plurality of discrete windows (e.g., non-overlapping chromosomal windows) of the reference genome to generate a first cfDNA set. The quantitative measure of the cfDNA sequencing reads may be counts of DNA sequencing reads that are aligned with a given discrete window (e.g., a non-overlapping chromosomal window). CfDNA sequencing reads having a portion or all of the sequencing read aligning with a given non-overlapping chromosomal window may be counted toward the quantitative measure for that non-overlapping chromosomal window.

In some embodiments, generation of a tumor load score may comprise generating a quantitative measure of the germline DNA sequencing reads for each of the plurality of non-overlapping chromosomal windows to generate a germline DNA set. The quantitative measure of the cfDNA sequencing reads may be counts of DNA sequencing reads that are aligned with a given discrete window (e.g., a non-overlapping chromosomal window). Germline DNA sequencing reads (e.g., buffy coat DNA sequencing reads and/or whole blood DNA sequencing reads) having a portion or all of the sequencing read aligning with a given non-overlapping chromosomal window may be counted toward the quantitative measure for that non-overlapping chromosomal window.

In some embodiments, generation of a tumor load score may comprise generating a first tumor load score based on a first set of ratio values, which first set of ratio values comprises, for each of the plurality of non-overlapping chromosomal windows, a ratio of the quantitative measure in the first cfDNA set to the quantitative measure in the germline DNA set, which first tumor load score is indicative of the tumor load for the subject.

The method of assessing tumor load may comprise comparing a first set of data corresponding to a first ratio set to a second set of data corresponding to a second ratio set, for example, comparing a cfDNA ratio set taken at a second time point to a germline ratio set taken at a first time point. Such a comparison may generate a tumor load score. Other possible comparisons may include, but are not limited to, a cfDNA ratio set taken at a first time point to a cfDNA ratio set taken at a second time point; a cfDNA ratio set taken at a first time point to a germline ratio set taken at a first time point; a cfDNA ratio set taken at a first time point to a germline ratio set taken at a second time point; a cfDNA ratio set taken at a second time point to a germline ratio taken at a second time point; a cfDNA ratio set taken at a second time point to a germline ratio taken at a first time point; a germline ratio set taken at a second time point to a germline ratio taken at a first time point; etc.

Generation of the tumor load score based on the set of ratio values may comprise performing a logarithm transformation of the set of ratio values to generate a set of log ratio values. Generation of the tumor load score based on the set of ratio values may comprise performing a summation of the first set of log ratio values. This summation may be a weighted sum (with different weights for each of the log ratio values in the set of log ratio values, or the same weight for each of the log ratio values in the set of log ratio values). Log ratio values may have a positive value when the number of cfDNA reads in a given non-overlapping chromosomal window is greater than the number of germline DNA reads in the non-overlapping chromosomal window (which may have an effect of increasing the tumor load score when included in the summation for the tumor load score). Log ratio values may have a negative value when the number of cfDNA reads in a given non-overlapping chromosomal window is less than the number of germline DNA reads in the non-overlapping chromosomal window (which may have an effect of decreasing the tumor load score when included in the summation for the tumor load score). Log ratio values may have a value of zero when the number of cfDNA reads in a given non-overlapping chromosomal window is equal to the number of germline DNA reads in the non-overlapping chromosomal window (which may have no effect of increasing or decreasing the tumor load score when included in the summation for the tumor load score).

Alternatively, generation of the tumor load score based on the set of ratio values may comprise performing a summation of the first set of ratio values. This summation may be a weighted sum (with different weights for each of the ratio values in the set of ratio values, or the same weight for each of the ratio values in the set of ratio values).

Alternatively, generation of the tumor load score based on the first set of ratio values may comprise performing a summation of the non-negative values of each of the set of log ratio values. This summation may be a weighted sum (with different weights for each of the ratio values in the set of ratio values, or the same weight for each of the ratio values in the set of ratio values). In this approach, the non-negative values of log ratio values may have a positive value when the number of cfDNA reads in a given non-overlapping chromosomal window is greater than the number of germline DNA reads in the non-overlapping chromosomal window (which may have an effect of increasing the tumor load score when included in the summation for the tumor load score). The non-negative values of log ratio values may have zero value when the number of cfDNA reads in a given non-overlapping chromosomal window is less than or equal to the number of germline DNA reads in the non-overlapping chromosomal window (which may have no effect of increasing or decreasing the tumor load score when included in the summation for the tumor load score). In this approach, only cfDNA reads with greater quantitative measures (e.g., counts) than the germline DNA reads in a given non-overlapping chromosomal window may have an effect of increasing the tumor load score when included in the summation for the tumor load score.

In some embodiments, the method of assessing tumor load further comprises determining whether the first tumor load score is greater than a predetermined threshold, wherein a first tumor load score greater than the predetermined threshold indicates a presence of a cancer in the subject. The predetermined threshold may be generated by performing the tumor load assessment (e.g., by generating a tumor load score) on one or more samples from one or more control subjects (e.g., patients known to have a certain tumor type, patients known to have a certain tumor type of a certain stage, or healthy subjects not exhibiting any cancer) and identifying a suitable predetermined threshold based on the tumor load assessments of the control samples. The predetermined threshold may be adjusted based on a desired sensitivity, specificity, positive predictive value (PPV), negative predictive value (NPV), or accuracy of detecting the tumor of one or more types. The predetermined threshold may be adjusted to be lower if a high sensitivity of cancer diagnosis is desired. The predetermined threshold may be adjusted to be higher if a high specificity of cancer diagnosis is desired. The predetermined threshold may be adjusted so as to maximize the area under curve (AUC) or a receiver operator characteristic (ROC) of the control samples obtained from the control subjects. The predetermined threshold may be adjusted so as to achieve a desired balance between false positives (FPs) and false negatives (FNs) in diagnosing cancer comprising a tumor of one or more types.

In some embodiments, the method of assessing tumor load further comprises determining whether the first tumor load score is greater than a predetermined threshold, wherein a first tumor load score greater than the predetermined threshold indicates a presence of a cancer in the subject. The predetermined threshold may be generated by performing the tumor load assessment (e.g., by generating a tumor load score) on one or more samples from one or more control subjects (e.g., patients known to have a certain tumor type, patients known to have a certain tumor type of a certain stage, or healthy subjects not exhibiting any cancer) and identifying a suitable predetermined threshold based on the tumor load assessments of the control samples. The predetermined threshold may be adjusted based on a desired sensitivity, specificity, positive predictive value (PPV), negative predictive value (NPV), or accuracy of detecting the tumor of one or more types. The predetermined threshold may be adjusted to be lower if a high sensitivity of cancer diagnosis is desired. The predetermined threshold may be adjusted to be higher if a high specificity of cancer diagnosis is desired. The predetermined threshold may be adjusted so as to maximize the area under curve (AUC) or a receiver operator characteristic (ROC) of the control samples obtained from the control subjects. The predetermined threshold may be adjusted so as to achieve a desired balance between false positives (FPs) and false negatives (FNs) in diagnosing cancer comprising a tumor of one or more types.

In some embodiments, the method of assessing tumor load further comprises: receiving sequencing information for cfDNA gathered at a second time point, the sequencing information from the second time point comprising second cfDNA sequencing reads; aligning the second cfDNA sequencing reads to the reference genome; generating a quantitative measure of the second cfDNA sequencing reads for each of the plurality of non-overlapping chromosomal windows to generate a second cfDNA set; and generating a second tumor load score based on a second set of ratio values, which second set of ratio values comprises, for each of the plurality of non-overlapping chromosomal windows, a ratio of the quantitative measure in the second cfDNA set to the quantitative measure in the germline DNA set. The second time point may be chosen for a suitable comparison of tumor load assessment relative to the first time point. Examples of second time points may correspond to a time after surgical resection, a time during treatment administration or after treatment administration to treat the cancer in the subject to monitor efficiency of the treatment, or a time after cancer is undetectable in the subject after treatment to monitor for residual disease or cancer recurrence in the subject. Any combination of cfDNA or germline DNA (buffy coat DNA and/or whole blood DNA) may be collected at the second, third, or subsequent time points for generation of second, third, or subsequent tumor load scores.

In some embodiments, the method of assessing tumor load further comprises determining a difference between the first tumor load score and the second tumor load score, which difference is indicative of a progression or regression of a tumor of the subject. Alternatively or in combination, the method may further comprise generating, by a computer processor, a plot of the first tumor load score and the second tumor load score as a function of the first time point and the second time point, which plot is indicative of the progression or regression of the tumor of the subject. For example, the computer processor may generate a plot of the two or more tumor load scores on a y-axis against the times corresponding to the time of collection for the data corresponding to the two or more load score on an x-axis.

A determined difference or a plot illustrating a difference between the first tumor load score and the second tumor load score may be indicative of a progression or regression of a tumor of the subject. If the second tumor load score is larger than the first tumor load score, that difference may indicate an increased tumor load (or tumor burden) in the subject, which may indicate, e.g., tumor progression, inefficacy of a treatment to the tumor in the subject, resistance of the tumor to an ongoing treatment, metastasis of the tumor to other sites in the subject, or residual disease or cancer recurrence in the subject. If the second tumor load score is smaller than the first tumor load score, that difference may indicate a decreased tumor load (or tumor burden) in the subject, which may indicate, e.g., tumor regression, efficacy of a surgical resection of the tumor in the subject, efficacy of a treatment to the tumor in the subject, or lack of residual disease or cancer recurrence in the subject.

In some embodiments, a tumor load score may be generated by computing a weighted sum of two, three, four, or more than four tumor load scores (e.g., by using different methods to generate tumor load scores as described elsewhere herein).

After assessing and/or monitoring tumor load of a subject to determine a diagnosis of a cancer, prognosis of a cancer, or an indication of progression or regression of a tumor in the subject, one or more clinical outcomes may be assigned based on the tumor load assessment (e.g., tumor load score) or monitoring (e.g., a difference between tumor load scores between two or more time points). Such clinical outcomes may include diagnosing the subject with a cancer comprising tumors of one or more types, diagnosing the subject with the cancer comprising tumors of one or more types and stages, prognosing the subject with the cancer (e.g., indicating a clinical course of treatment (e.g., surgery, chemotherapy, radiotherapy, immunotherapy, or other treatment) for the subject, indicating another clinical course of action (e.g., no treatment, continued monitoring such as on a prescribed time interval basis, stopping a current treatment, switching to another treatment), or indicating an expected survival time for the subject.

B. Methods for Assessing Tumor Load Using Non-Overlapping Repetitive Element Windows Also disclosed herein is a method for assessing a tumor load for a subject, the method comprising: receiving sequencing information for cell-free DNA (cfDNA) from the subject gathered at a first time point and sequencing information for germline DNA from the subject, the sequencing information comprising first cfDNA sequencing reads and germline DNA sequencing reads; aligning the first cfDNA sequencing reads to a reference genome; aligning the germline DNA sequencing reads to the reference genome; generating a quantitative measure of the first cfDNA sequencing reads for each of a plurality of non-overlapping repetitive element windows of the reference genome to generate a first cfDNA set; generating a quantitative measure of the germline DNA sequencing reads for each of the plurality of non-overlapping repetitive element windows to generate a germline DNA set; and generating a first tumor load score based on a first set of ratio values, which first set of ratio values comprises, for each of the plurality of non-overlapping repetitive element windows, a ratio of the quantitative measure in the first cfDNA set to the quantitative measure in the germline DNA set, which first tumor load score is indicative of the tumor load for the subject.

In some embodiments, generation of a tumor load score may comprise receiving sequencing information for cell-free DNA (cfDNA) from the subject gathered at a first time point from the subject, the sequencing information comprising first cfDNA sequencing reads. Any of the first, second, third, or subsequent time points may correspond to any time point during the course of diagnosis, prognosis, or treatment of a cancer in the subject (e.g., diagnosing a cancer comprising one or more tumor types in the subject, prognosing a cancer comprising one or more tumor types in the subject, before initiating a course of treatment (e.g., surgical resection, chemotherapy, radiotherapy, immunotherapy, targeted therapy) to treat the cancer in the subject, during the course of treatment, before initiating a second, third, or other subsequent course of treatment, or during the course of the second, third or other subsequent course of treatment to treat the cancer in the subject). Sequencing reads may be generated from the cfDNA using any suitable sequencing method known to one of skill in the art.

In some embodiments, generation of a tumor load score may comprise receiving sequencing information for germline DNA from the subject, the sequencing information comprising germline DNA sequencing reads. Germline DNA may comprise buffy coat DNA and/or whole blood DNA. Germline DNA sequencing reads may be comprise sequencing reads of the buffy coat DNA and/or the whole blood DNA. Germline DNA may be acquired from the same sample from which cfDNA is obtained, or may be acquired from another sample at the same time point from which cfDNA is obtained, or may be acquired from a sample different from the sample from which cfDNA is obtained at the same time point, or may be acquired from a sample different from the sample from which cfDNA is obtained at a different time point.

In some embodiments, generation of a tumor load score may comprise aligning the first cfDNA sequencing reads to a reference genome. The reference genome may comprise at least a portion of a genome (e.g., the human genome). The reference genome may comprise an entire genome (e.g., the entire human genome). The reference genome may comprise a database comprising a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and repetitive elements (LINEs, SINEs, and/or low copy repeats)). The alignment may be performed using a Burrows-Wheeler algorithm or any other alignment algorithm known to one who is skilled in the art.

In some embodiments, generation of a tumor load score may comprise aligning the germline DNA sequencing reads to a reference genome. The reference genome may comprise at least a portion of a genome (e.g., the human genome). The reference genome may comprise an entire genome (e.g., the entire human genome). The reference genome may comprise a database comprising a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and repetitive elements (LINEs, SINEs, and/or low copy repeats)). The alignment may be performed using a Burrows-Wheeler algorithm or any other alignment algorithm known to one who is skilled in the art. The cfDNA sequencing reads and the germline DNA sequencing reads may be aligned to the same reference genome or different reference genomes.

In some embodiments, generation of a tumor load score may comprise generating a quantitative measure of the first cfDNA sequencing reads for each of a plurality of discrete windows (e.g., non-overlapping repetitive element windows) of the reference genome to generate a first cfDNA set. The quantitative measure of the cfDNA sequencing reads may be counts of DNA sequencing reads that are aligned with a given discrete window (e.g., a non-overlapping repetitive element window). CfDNA sequencing reads having a portion or all of the sequencing read aligning with a given non-overlapping repetitive element window may be counted toward the quantitative measure for that non-overlapping repetitive element window.

In some embodiments, the plurality of non-overlapping repetitive element windows are selected from the group consisting of Short Interspersed Elements (SINEs), Long Interspersed Elements (LINEs), and low copy repeats. These SINEs, LINEs, and low copy repeats may include any of a number of retrotransposon families (e.g., those previously associated with one or more cancer types). For example, LINE-1 and SINE1 B1 retrotransposon families have been found to be up-regulated and undergo copy number amplification during breast cancer tumor progression. Similarly, SINEs in the Alu family of repetitive elements (which are about 300 bp long) are known to correlate with many diseases including cancer. For example, Alu insertions have been linked to breast cancer, hypercholesteremia, hemophilia, and type II diabetes mellitus, while Alu single nucleotide variants (SNVs) have been linked to lung cancer, gastric cancer, and Alzheimer's disease. Patterns of specific and non-specific repetitive elements such as SINEs, LINEs, and low copy repeats may be indicative of tumor load. Changes over time in these patterns of repetitive elements may be indicative of changes in tumor load.

In some embodiments, the plurality of non-overlapping repetitive element windows selected from the group consisting of SINEs, LINEs, and low copy repeats comprises at least two, at least three, at least four, or more than four distinct repetitive elements.

In some embodiments, each of the plurality of non-overlapping repetitive element windows comprises a predetermined size of a number of base pairs.

In some embodiments, generation of a tumor load score may comprise generating a quantitative measure of the germline DNA sequencing reads for each of the plurality of non-overlapping repetitive element windows to generate a germline DNA set. The quantitative measure of the cfDNA sequencing reads may be counts of DNA sequencing reads that are aligned with a given discrete window (e.g., a non-overlapping repetitive element window). Germline DNA sequencing reads (e.g., buffy coat DNA sequencing reads and/or whole blood DNA sequencing reads) having a portion or all of the sequencing read aligning with a given non-overlapping repetitive element window may be counted toward the quantitative measure for that non-overlapping repetitive element window.

In some embodiments, generation of a tumor load score may comprise generating a first tumor load score based on a first set of ratio values, which first set of ratio values comprises, for each of the plurality of non-overlapping repetitive element windows, a ratio of the quantitative measure in the first cfDNA set to the quantitative measure in the germline DNA set, which first tumor load score is indicative of the tumor load for the subject.

The method of assessing tumor load may comprise comparing a first set of data corresponding to a first ratio set to a second set of data corresponding to a second ratio set, for example, comparing a cfDNA ratio set taken at a second time point to a germline ratio set taken at a first time point. Such a comparison may generate a tumor load score. One of skill in the art will appreciate other possible comparison including but not limited to a cfDNA ratio set taken at a first time point to a cfDNA ratio set taken at a second time point; a cfDNA ratio set taken at a first time point to a germline ratio set taken at a first time point; a cfDNA ratio set taken at a first time point to a germline ratio set taken at a second time point; a cfDNA ratio set taken at a second time point to a germline ratio taken at a second time point; a cfDNA ratio set taken at a second time point to a germline ratio taken at a first time point; a germline ratio set taken at a second time point to a germline ratio taken at a first time point; etc.

Generation of the tumor load score based on the set of ratio values may comprise performing a logarithm transformation of the set of ratio values to generate a set of log ratio values. Generation of the tumor load score based on the set of ratio values may comprise performing a summation of the first set of log ratio values. This summation may be a weighted sum (with different weights for each of the log ratio values in the set of log ratio values, or the same weight for each of the log ratio values in the set of log ratio values). Log ratio values may have a positive value when the number of cfDNA reads in a given non-overlapping repetitive element window is greater than the number of germline DNA reads in the non-overlapping repetitive element window (which may have an effect of increasing the tumor load score when included in the summation for the tumor load score). Log ratio values may have a negative value when the number of cfDNA reads in a given non-overlapping repetitive element window is less than the number of germline DNA reads in the non-overlapping repetitive element window (which may have an effect of decreasing the tumor load score when included in the summation for the tumor load score). Log ratio values may have a value of zero when the number of cfDNA reads in a given non-overlapping repetitive element window is equal to the number of germline DNA reads in the non-overlapping repetitive element window (which may have no effect of increasing or decreasing the tumor load score when included in the summation for the tumor load score).

Alternatively, generation of the tumor load score based on the set of ratio values may comprise performing a summation of the first set of ratio values. This summation may be a weighted sum (with different weights for each of the ratio values in the set of ratio values, or the same weight for each of the ratio values in the set of ratio values).

Alternatively, generation of the tumor load score based on the first set of ratio values may comprise performing a summation of the non-negative values of each of the set of log ratio values. This summation may be a weighted sum (with different weights for each of the ratio values in the set of ratio values, or the same weight for each of the ratio values in the set of ratio values). In this approach, the non-negative values of log ratio values may have a positive value when the number of cfDNA reads in a given non-overlapping repetitive element window is greater than the number of germline DNA reads in the non-overlapping repetitive element window (which may have an effect of increasing the tumor load score when included in the summation for the tumor load score). The non-negative values of log ratio values may have zero value when the number of cfDNA reads in a given non-overlapping repetitive element window is less than or equal to the number of germline DNA reads in the non-overlapping repetitive element window (which may have no effect of increasing or decreasing the tumor load score when included in the summation for the tumor load score). In this approach, only cfDNA reads with greater quantitative measures (e.g., counts) than the germline DNA reads in a given non-overlapping repetitive element window may have an effect of increasing the tumor load score when included in the summation for the tumor load score.

In some embodiments, the method of assessing tumor load further comprises determining whether the first tumor load score is greater than a predetermined threshold, wherein a first tumor load score greater than the predetermined threshold indicates a presence of a cancer in the subject. The predetermined threshold may be generated by performing the tumor load assessment (e.g., by generating a tumor load score) on one or more samples from one or more control subjects (e.g., patients known to have a certain tumor type, patients known to have a certain tumor type of a certain stage, or healthy subjects not exhibiting any cancer) and identifying a suitable predetermined threshold based on the tumor load assessments of the control samples. The predetermined threshold may be adjusted based on a desired sensitivity, specificity, positive predictive value (PPV), negative predictive value (NPV), or accuracy of detecting the tumor of one or more types. The predetermined threshold may be adjusted to be lower if a high sensitivity of cancer diagnosis is desired. The predetermined threshold may be adjusted to be higher if a high specificity of cancer diagnosis is desired. The predetermined threshold may be adjusted so as to maximize the area under curve (AUC) or a receiver operator characteristic (ROC) of the control samples obtained from the control subjects. The predetermined threshold may be adjusted so as to achieve a desired balance between false positives (FPs) and false negatives (FNs) in diagnosing cancer comprising a tumor of one or more types.

In some embodiments, the method of assessing tumor load further comprises determining whether the first tumor load score is greater than a predetermined threshold, wherein a first tumor load score greater than the predetermined threshold indicates a presence of a cancer in the subject. The predetermined threshold may be generated by performing the tumor load assessment (e.g., by generating a tumor load score) on one or more samples from one or more control subjects (e.g., patients known to have a certain tumor type, patients known to have a certain tumor type of a certain stage, or healthy subjects not exhibiting any cancer) and identifying a suitable predetermined threshold based on the tumor load assessments of the control samples. The predetermined threshold may be adjusted based on a desired sensitivity, specificity, positive predictive value (PPV), negative predictive value (NPV), or accuracy of detecting the tumor of one or more types. The predetermined threshold may be adjusted to be lower if a high sensitivity of cancer diagnosis is desired. The predetermined threshold may be adjusted to be higher if a high specificity of cancer diagnosis is desired. The predetermined threshold may be adjusted so as to maximize the area under curve (AUC) or a receiver operator characteristic (ROC) of the control samples obtained from the control subjects. The predetermined threshold may be adjusted so as to achieve a desired balance between false positives (FPs) and false negatives (FNs) in diagnosing cancer comprising a tumor of one or more types.

In some embodiments, the method of assessing tumor load further comprises: receiving sequencing information for cfDNA gathered at a second time point, the sequencing information from the second time point comprising second cfDNA sequencing reads; aligning the second cfDNA sequencing reads to the reference genome; generating a quantitative measure of the second cfDNA sequencing reads for each of the plurality of non-overlapping repetitive element windows to generate a second cfDNA set; and generating a second tumor load score based on a second set of ratio values, which second set of ratio values comprises, for each of the plurality of non-overlapping repetitive element windows, a ratio of the quantitative measure in the second cfDNA set to the quantitative measure in the germline DNA set. The second time point may be chosen for a suitable comparison of tumor load assessment relative to the first time point. Examples of second time points may correspond to a time after surgical resection, a time during treatment administration or after treatment administration to treat the cancer in the subject to monitor efficiency of the treatment, or a time after cancer is undetectable in the subject after treatment to monitor for residual disease or cancer recurrence in the subject. Any combination of cfDNA or germline DNA (buffy coat DNA and/or whole blood DNA) may be collected at the second, third, or subsequent time points for generation of second, third, or subsequent tumor load scores.

In some embodiments, the method of assessing tumor load further comprises determining a difference between the first tumor load score and the second tumor load score, which difference is indicative of a progression or regression of a tumor of the subject. Alternatively or in combination, the method may further comprise generating, by a computer processor, a plot of the first tumor load score and the second tumor load score as a function of the first time point and the second time point, which plot is indicative of the progression or regression of the tumor of the subject. For example, the computer processor may generate a plot of the two or more tumor load scores on a y-axis against the times corresponding to the time of collection for the data corresponding to the two or more load score on an x-axis.

A determined difference or a plot illustrating a difference between the first tumor load score and the second tumor load score may be indicative of a progression or regression of a tumor of the subject. If the second tumor load score is larger than the first tumor load score, that difference may indicate an increased tumor load (or tumor burden) in the subject, which may indicate, e.g., tumor progression, inefficacy of a treatment to the tumor in the subject, resistance of the tumor to an ongoing treatment, metastasis of the tumor to other sites in the subject, or residual disease or cancer recurrence in the subject. If the second tumor load score is smaller than the first tumor load score, that difference may indicate a decreased tumor load (or tumor burden) in the subject, which may indicate, e.g., tumor regression, efficacy of a surgical resection of the tumor in the subject, efficacy of a treatment to the tumor in the subject, or lack of residual disease or cancer recurrence in the subject.

In some embodiments, a tumor load score may be generated by computing a weighted sum of two, three, four, or more than four tumor load scores (e.g., by using different methods to generate tumor load scores as described elsewhere herein).

After assessing and/or monitoring tumor load of a subject to determine a diagnosis of a cancer, prognosis of a cancer, or an indication of progression or regression of a tumor in the subject, one or more clinical outcomes may be assigned based on the tumor load assessment (e.g., tumor load score) or monitoring (e.g., a difference between tumor load scores between two or more time points). Such clinical outcomes may include diagnosing the subject with a cancer comprising tumors of one or more types, diagnosing the subject with the cancer comprising tumors of one or more types and stages, prognosing the subject with the cancer (e.g., indicating a clinical course of treatment (e.g., surgery, chemotherapy, radiotherapy, immunotherapy, or other treatment) for the subject, indicating another clinical course of action (e.g., no treatment, continued monitoring such as on a prescribed time interval basis, stopping a current treatment, switching to another treatment), or indicating an expected survival time for the subject.

C. Methods for Tumor Load Measurement Via Database of Repetitive Element Windows Also disclosed herein is a method for assessing a tumor load for a subject, the method comprising: receiving sequencing information for cell-free DNA (cfDNA) from the subject gathered at a first time point and sequencing information for germline DNA from the subject, the sequencing information comprising first cfDNA sequencing reads and germline DNA sequencing reads; aligning the first cfDNA sequencing reads to a plurality of repetitive element windows from a database of repetitive element windows; aligning the germline DNA sequencing reads to the plurality of repetitive element windows; generating a quantitative measure of the first cfDNA sequencing reads for each of the plurality of repetitive element windows to generate a first cfDNA set; generating a quantitative measure of the germline DNA sequencing reads for each of the plurality of repetitive element windows to generate a germline DNA set; and generating a first tumor load score based on a first set of ratio values, which first set of ratio values comprises, for each of the plurality of repetitive element windows, a ratio of the quantitative measure in the first cfDNA set to the quantitative measure in the germline DNA set, which tumor load score is indicative of the tumor load for the subject.

In some embodiments, generation of a tumor load score may comprise receiving sequencing information for cell-free DNA (cfDNA) from the subject gathered at a first time point from the subject, the sequencing information comprising first cfDNA sequencing reads. Any of the first, second, third, or subsequent time points may correspond to any time point during the course of diagnosis, prognosis, or treatment of a cancer in the subject (e.g., diagnosing a cancer comprising one or more tumor types in the subject, prognosing a cancer comprising one or more tumor types in the subject, before initiating a course of treatment (e.g., surgical resection, chemotherapy, radiotherapy, immunotherapy, targeted therapy) to treat the cancer in the subject, during the course of treatment, before initiating a second, third, or other subsequent course of treatment, or during the course of the second, third or other subsequent course of treatment to treat the cancer in the subject). Sequencing reads may be generated from the cfDNA using any suitable sequencing method known to one of skill in the art.

In some embodiments, generation of a tumor load score may comprise receiving sequencing information for germline DNA from the subject, the sequencing information comprising germline DNA sequencing reads. Germline DNA may comprise buffy coat DNA and/or whole blood DNA. Germline DNA sequencing reads may be comprise sequencing reads of the buffy coat DNA and/or the whole blood DNA. Germline DNA may be acquired from the same sample from which cfDNA is obtained, or may be acquired from another sample at the same time point from which cfDNA is obtained, or may be acquired from a sample different from the sample from which cfDNA is obtained at the same time point, or may be acquired from a sample different from the sample from which cfDNA is obtained at a different time point.

In some embodiments, generation of a tumor load score may comprise aligning the first cfDNA sequencing reads to a plurality of repetitive element windows from a database of repetitive element windows. The database of repetitive element windows may comprise a plurality of repetitive element windows (e.g., derived from a genome such as the human genome, with or without applying one or more variants to such repetitive elements). The database may comprise a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and repetitive elements (LINEs, SINEs, and/or low copy repeats)). The alignment may be performed using a Burrows-Wheeler algorithm or any other alignment algorithm known to one who is skilled in the art.

In some embodiments, generation of a tumor load score may comprise aligning the germline DNA sequencing reads to a reference genome. The reference genome may comprise at least a portion of a genome (e.g., the human genome). The reference genome may comprise an entire genome (e.g., the entire human genome). The reference genome may comprise a database comprising a plurality of genomic regions that correspond to coding and/or non-coding genomic regions of a genome. The database may comprise a plurality of genomic regions that correspond to cancer-associated (or tumor-associated) coding and/or non-coding genomic regions of a genome, such as cancer driver mutations (e.g., single nucleotide variants (SNVs), copy number variants (CNVs), insertions or deletions (indels), fusion genes, and repetitive elements (LINEs, SINEs, and/or low copy repeats)). The alignment may be performed using a Burrows-Wheeler algorithm or any other alignment algorithm known to one who is skilled in the art. The cfDNA sequencing reads and the germline DNA sequencing reads may be aligned to the same reference genome or different reference genomes.

In some embodiments, generation of a tumor load score may comprise generating a quantitative measure of the first cfDNA sequencing reads for each of the plurality of repetitive element windows from the database of repetitive element windows to generate a first cfDNA set. The quantitative measure of the cfDNA sequencing reads may be counts of DNA sequencing reads that are aligned with a given discrete window (e.g., a repetitive element window from the database of repetitive element windows). CfDNA sequencing reads having a portion or all of the sequencing read aligning with a given repetitive element windows from the database of repetitive element windows may be counted toward the quantitative measure for that repetitive element window from the database of repetitive element windows.

In some embodiments, the plurality of repetitive element windows from the database of repetitive element windows are selected from the group consisting of Short Interspersed Elements (SINEs), Long Interspersed Elements (LINEs), and low copy repeats. These SINEs, LINEs, and low copy repeats may include any of a number of retrotransposon families (e.g., those previously associated with one or more cancer types). For example, LINE-1 and SINE1 B1 retrotransposon families have been found to be up-regulated and undergo copy number amplification during breast cancer tumor progression. Patterns of specific and non-specific repetitive elements such as SINEs, LINEs, and low copy repeats may be indicative of tumor load. Changes over time in these patterns of repetitive elements may be indicative of changes in tumor load.

In some embodiments, the plurality of repetitive element windows from the database of repetitive element windows selected from the group consisting of SINEs, LINEs, and low copy repeats comprises at least two, at least three, at least four, or more than four distinct repetitive elements.

In some embodiments, each of the plurality of repetitive element windows from the database of repetitive element windows comprises a predetermined size of a number of base pairs.

In some embodiments, generation of a tumor load score may comprise generating a quantitative measure of the germline DNA sequencing reads for each of the plurality of repetitive element windows from the database of repetitive element windows to generate a germline DNA set. The quantitative measure of the cfDNA sequencing reads may be counts of DNA sequencing reads that are aligned with a given discrete window (e.g., a repetitive element window from the database of repetitive element windows). Germline DNA sequencing reads (e.g., buffy coat DNA sequencing reads and/or whole blood DNA sequencing reads) having a portion or all of the sequencing read aligning with a given repetitive element window from the database of repetitive element windows may be counted toward the quantitative measure for that repetitive element window from the database of repetitive element windows.

In some embodiments, generation of a tumor load score may comprise generating a first tumor load score based on a first set of ratio values, which first set of ratio values comprises, for each of the plurality of repetitive element windows from the database of repetitive element windows, a ratio of the quantitative measure in the first cfDNA set to the quantitative measure in the germline DNA set, which first tumor load score is indicative of the tumor load for the subject.

The method of assessing tumor load may comprise comparing a first set of data corresponding to a first ratio set to a second set of data corresponding to a second ratio set, for example, comparing a cfDNA ratio set taken at a second time point to a germline ratio set taken at a first time point. Such a comparison may generate a tumor load score. One of skill in the art will appreciate other possible comparison including but not limited to a cfDNA ratio set taken at a first time point to a cfDNA ratio set taken at a second time point; a cfDNA ratio set taken at a first time point to a germline ratio set taken at a first time point; a cfDNA ratio set taken at a first time point to a germline ratio set taken at a second time point; a cfDNA ratio set taken at a second time point to a germline ratio taken at a second time point; a cfDNA ratio set taken at a second time point to a germline ratio taken at a first time point; a germline ratio set taken at a second time point to a germline ratio taken at a first time point; etc.

Generation of the tumor load score based on the set of ratio values may comprise performing a logarithm transformation of the set of ratio values to generate a set of log ratio values. Generation of the tumor load score based on the set of ratio values may comprise performing a summation of the first set of log ratio values. This summation may be a weighted sum (with different weights for each of the log ratio values in the set of log ratio values, or the same weight for each of the log ratio values in the set of log ratio values). Log ratio values may have a positive value when the number of cfDNA reads in a given non-overlapping repetitive element window is greater than the number of germline DNA reads in the non-overlapping repetitive element window (which may have an effect of increasing the tumor load score when included in the summation for the tumor load score). Log ratio values may have a negative value when the number of cfDNA reads in a given non-overlapping repetitive element window is less than the number of germline DNA reads in the non-overlapping repetitive element window (which may have an effect of decreasing the tumor load score when included in the summation for the tumor load score). Log ratio values may have a value of zero when the number of cfDNA reads in a given non-overlapping repetitive element window is equal to the number of germline DNA reads in the non-overlapping repetitive element window (which may have no effect of increasing or decreasing the tumor load score when included in the summation for the tumor load score).

Alternatively, generation of the tumor load score based on the set of ratio values may comprise performing a summation of the first set of ratio values. This summation may be a weighted sum (with different weights for each of the ratio values in the set of ratio values, or the same weight for each of the ratio values in the set of ratio values).

Alternatively, generation of the tumor load score based on the first set of ratio values may comprise performing a summation of the non-negative values of each of the set of log ratio values. This summation may be a weighted sum (with different weights for each of the ratio values in the set of ratio values, or the same weight for each of the ratio values in the set of ratio values). In this approach, the non-negative values of log ratio values may have a positive value when the number of cfDNA reads in a given repetitive element window from the database of repetitive element windows is greater than the number of germline DNA reads in the plurality of repetitive element windows from the database of repetitive element windows (which may have an effect of increasing the tumor load score when included in the summation for the tumor load score). The non-negative values of log ratio values may have zero value when the number of cfDNA reads in a given repetitive element window from the database of repetitive element windows is less than or equal to the number of germline DNA reads in the repetitive element window from the database of repetitive element windows (which may have no effect of increasing or decreasing the tumor load score when included in the summation for the tumor load score). In this approach, only cfDNA reads with greater quantitative measures (e.g., counts) than the germline DNA reads in a given repetitive element window from the database of repetitive element windows may have an effect of increasing the tumor load score when included in the summation for the tumor load score.

In some embodiments, the method of assessing tumor load further comprises determining whether the first tumor load score is greater than a predetermined threshold, wherein a first tumor load score greater than the predetermined threshold indicates a presence of a cancer in the subject. The predetermined threshold may be generated by performing the tumor load assessment (e.g., by generating a tumor load score) on one or more samples from one or more control subjects (e.g., patients known to have a certain tumor type, patients known to have a certain tumor type of a certain stage, or healthy subjects not exhibiting any cancer) and identifying a suitable predetermined threshold based on the tumor load assessments of the control samples. The predetermined threshold may be adjusted based on a desired sensitivity, specificity, positive predictive value (PPV), negative predictive value (NPV), or accuracy of detecting the tumor of one or more types. The predetermined threshold may be adjusted to be lower if a high sensitivity of cancer diagnosis is desired. The predetermined threshold may be adjusted to be higher if a high specificity of cancer diagnosis is desired. The predetermined threshold may be adjusted so as to maximize the area under curve (AUC) or a receiver operator characteristic (ROC) of the control samples obtained from the control subjects. The predetermined threshold may be adjusted so as to achieve a desired balance between false positives (FPs) and false negatives (FNs) in diagnosing cancer comprising a tumor of one or more types.

In some embodiments, the method of assessing tumor load further comprises determining whether the first tumor load score is greater than a predetermined threshold, wherein a first tumor load score greater than the predetermined threshold indicates a presence of a cancer in the subject. The predetermined threshold may be generated by performing the tumor load assessment (e.g., by generating a tumor load score) on one or more samples from one or more control subjects (e.g., patients known to have a certain tumor type, patients known to have a certain tumor type of a certain stage, or healthy subjects not exhibiting any cancer) and identifying a suitable predetermined threshold based on the tumor load assessments of the control samples. The predetermined threshold may be adjusted based on a desired sensitivity, specificity, positive predictive value (PPV), negative predictive value (NPV), or accuracy of detecting the tumor of one or more types. The predetermined threshold may be adjusted to be lower if a high sensitivity of cancer diagnosis is desired. The predetermined threshold may be adjusted to be higher if a high specificity of cancer diagnosis is desired. The predetermined threshold may be adjusted so as to maximize the area under curve (AUC) or a receiver operator characteristic (ROC) of the control samples obtained from the control subjects. The predetermined threshold may be adjusted so as to achieve a desired balance between false positives (FPs) and false negatives (FNs) in diagnosing cancer comprising a tumor of one or more types.

In some embodiments, the method of assessing tumor load further comprises: receiving sequencing information for cfDNA gathered at a second time point, the sequencing information from the second time point comprising second cfDNA sequencing reads; aligning the second cfDNA sequencing reads to the plurality of repetitive element windows from the database of repetitive element windows; generating a quantitative measure of the second cfDNA sequencing reads for each of the plurality of repetitive element windows from the database of repetitive element windows to generate a second cfDNA set; and generating a second tumor load score based on a second set of ratio values, which second set of ratio values comprises, for each of the plurality of repetitive element windows from the database of repetitive element windows, a ratio of the quantitative measure in the second cfDNA set to the quantitative measure in the germline DNA set. The second time point may be chosen for a suitable comparison of tumor load assessment relative to the first time point. Examples of second time points may correspond to a time after surgical resection, a time during treatment administration or after treatment administration to treat the cancer in the subject to monitor efficiency of the treatment, or a time after cancer is undetectable in the subject after treatment to monitor for residual disease or cancer recurrence in the subject. Any combination of cfDNA or germline DNA (buffy coat DNA and/or whole blood DNA) may be collected at the second, third, or subsequent time points for generation of second, third, or subsequent tumor load scores.

In some embodiments, the method of assessing tumor load further comprises determining a difference between the first tumor load score and the second tumor load score, which difference is indicative of a progression or regression of a tumor of the subject. Alternatively or in combination, the method may further comprise generating, by a computer processor, a plot of the first tumor load score and the second tumor load score as a function of the first time point and the second time point, which plot is indicative of the progression or regression of the tumor of the subject. For example, the computer processor may generate a plot of the two or more tumor load scores on a y-axis against the times corresponding to the time of collection for the data corresponding to the two or more load score on an x-axis.

A determined difference or a plot illustrating a difference between the first tumor load score and the second tumor load score may be indicative of a progression or regression of a tumor of the subject. If the second tumor load score is larger than the first tumor load score, that difference may indicate an increased tumor load (or tumor burden) in the subject, which may indicate, e.g., tumor progression, inefficacy of a treatment to the tumor in the subject, resistance of the tumor to an ongoing treatment, metastasis of the tumor to other sites in the subject, or residual disease or cancer recurrence in the subject. If the second tumor load score is smaller than the first tumor load score, that difference may indicate a decreased tumor load (or tumor burden) in the subject, which may indicate, e.g., tumor regression, efficacy of a surgical resection of the tumor in the subject, efficacy of a treatment to the tumor in the subject, or lack of residual disease or cancer recurrence in the subject.

In some embodiments, a tumor load score may be generated by computing a weighted sum of two, three, four, or more than four tumor load scores (e.g., by using different methods to generate tumor load scores as described elsewhere herein).

After assessing and/or monitoring tumor load of a subject to determine a diagnosis of a cancer, prognosis of a cancer, or an indication of progression or regression of a tumor in the subject, one or more clinical outcomes may be assigned based on the tumor load assessment (e.g., tumor load score) or monitoring (e.g., a difference between tumor load scores between two or more time points). Such clinical outcomes may include diagnosing the subject with a cancer comprising tumors of one or more types, diagnosing the subject with the cancer comprising tumors of one or more types and stages, prognosing the subject with the cancer (e.g., indicating a clinical course of treatment (e.g., surgery, chemotherapy, radiotherapy, immunotherapy, or other treatment) for the subject, indicating another clinical course of action (e.g., no treatment, continued monitoring such as on a prescribed time interval basis, stopping a current treatment, switching to another treatment), or indicating an expected survival time for the subject.

FIGURE DESCRIPTIONS

FIG. 1 illustrates an example of isolation of three types of DNA sources (plasma containing cfDNA, buffy coat containing germline DNA, and whole blood containing mostly germline DNA with some cfDNA) from a blood sample tube, in accordance with some embodiments. In particular, FIG. 1 illustrates the isolation of plasma, buffy coat, and whole blood from tubes of blood samples. As seen in FIG. 1, a first tube of blood sample has been collected (e.g., using a Streck collection tube) separated into plasma in the top portion, buffy coat in the middle portion, and red blood cells in the bottom portion. The tube of blood sample can be separated by centrifugation, e.g., density gradient centrifugation under conditions sufficient to achieve separation of these three components into separate layers. The plasma comprises cfDNA and the buffy coat comprises white blood cells that contain germline DNA. Additionally, FIG. 1 illustrates a second tube of blood sample that has been collected (e.g., using an EDTA collection tube) comprising whole blood (comprising plasma, serum, and white blood cells) containing mostly germline DNA with some cfDNA. The collected cfDNA ("CB"), buffy coat DNA ("BC"), and/or whole blood DNA ("WB") can be used for sequencing purposes to extract cfDNA sequencing reads, buffy coat DNA sequencing reads, and/or whole blood DNA sequencing reads, respectively. CfDNA sequencing information may be obtained by obtaining a sample from the subject, isolating cfDNA from the sample, and sequencing the isolated cfDNA to produce the cfDNA sequencing reads. Germline DNA sequencing information may be obtained by obtaining a sample from the subject, isolating buffy coat DNA and/or whole blood DNA from the sample, and sequencing the isolated buffy coat DNA and/or whole blood DNA to produce the germline DNA sequencing reads. The sequencing information may be obtained by subjecting cell-free nucleic acids of the subject to untargeted sequencing. The untargeted sequencing may comprise use of random primers. The sample may be a blood sample. The method of assessing tumor load may comprise generating a first library for use in the sequencing of the cfDNA. The method of assessing tumor load may comprise generating a second library for use in the sequencing of the germline DNA (e.g., buffy coat DNA and/or whole blood DNA).

In some embodiments, there are several possible bioinformatic methods: 1. Align reads from each sample type (cfDNA and germline DNA (comprising buffy coat DNA and/or whole blood DNA)) to a human genome sequence and determine quantitative measures (e.g., counts) for numbers of reads found in each chromosome subdivided into smaller windows for the comparison of read ratios amongst sample types. 2. Align reads from each sample type (cfDNA and germline DNA (comprising buffy coat DNA and/or whole blood DNA)) to the human genome sequence and determine quantitative measures (e.g., counts) for numbers of read found only in repeat sequence regions (e.g., repetitive elements such as SINEs, LINEs, and low copy repeats) identified on each chromosome for the comparison of read ratios amongst sample types. 3. Align reads from each sample type (cfDNA and germline DNA (comprising buffy coat DNA and/or whole blood DNA)) to database of repeat sequence regions (SINE, LINE and low copy repeats) in the absence of the surrounding human genome sequence for the comparison of read ratios amongst sample types. Each of these approaches can yield slightly different and/or complementary results for tumor loads, any combination of which can be performed and combined into the tumor load score for tumor load assessment and monitoring.

Figure 2:
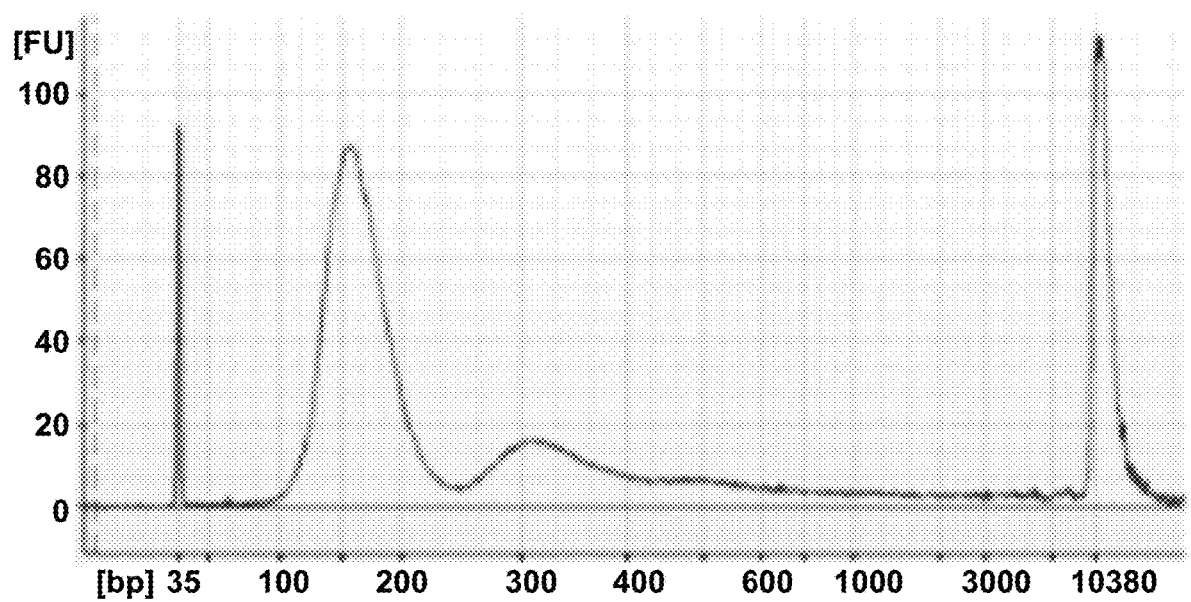
FIG. 2 illustrates an expected frequency distribution of fragment length (in base pairs, bp) of isolated cfDNA (also referred to as size distribution), in accordance with some embodiments.

FIG. 2 illustrates an expected frequency distribution of fragment length (in base pairs, bp) of isolated cfDNA (also referred to as size distribution), in accordance with some embodiments. In particular, the graph in FIG. 2 illustrates at least four modes in the size distribution: a peak at or around 35 bp (a marker/ladder), a main peak for cfDNA around 170-180 bp, a secondary peak for cfDNA around 320 bp, and a peak around 10380 bp (10 kilobases (kb), likely due to contaminating cellular DNA). This size distribution of cfDNA fragments may be used to validate the blood collection, DNA extraction, and DNA sequencing processes, as well as for designing, for example, the size of non-overlapping discrete windows for use in assessing tumor load and/or generating tumor load scores from analysis of cfDNA from a sample of a subject.

Figure 3:
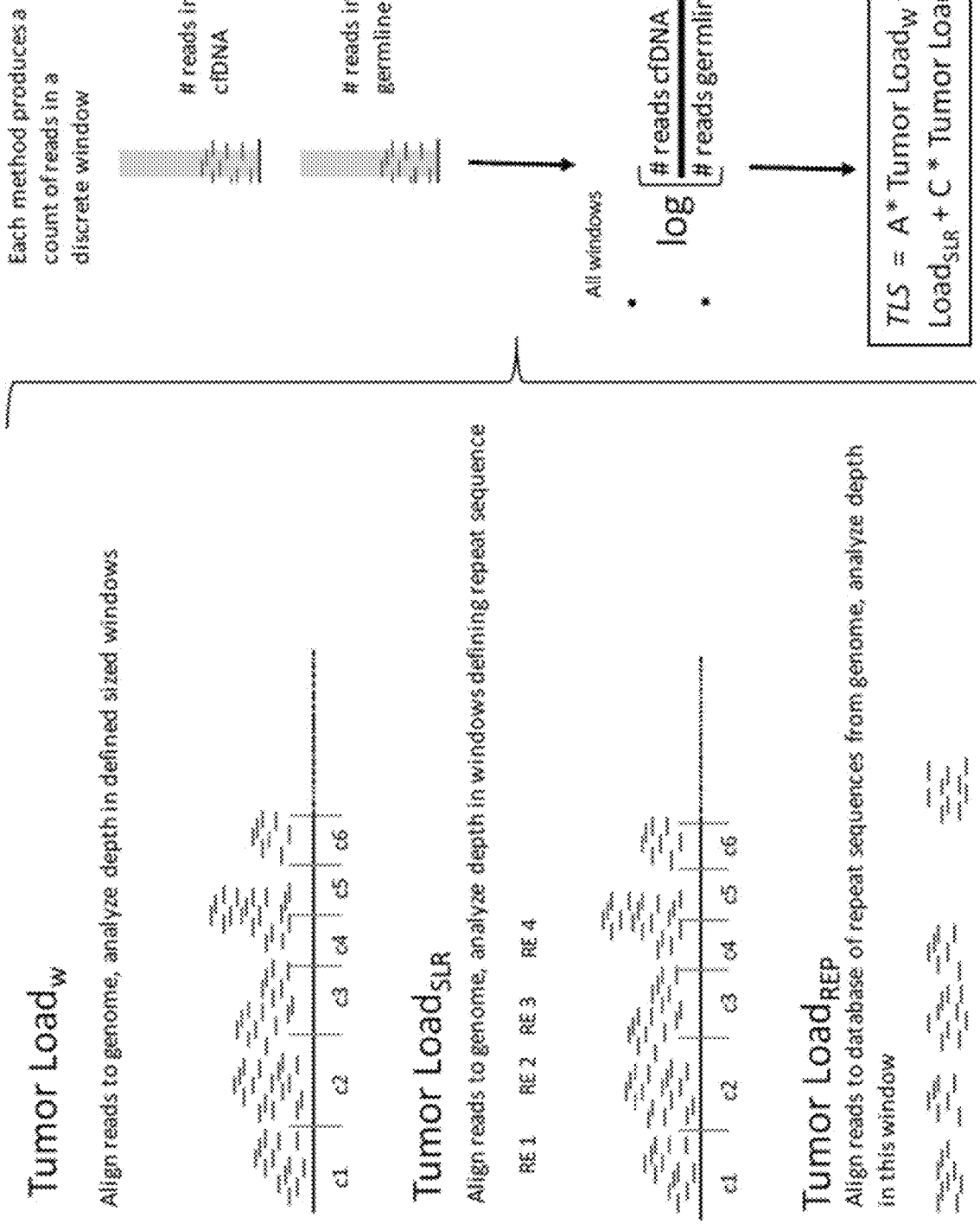
FIG. 3 illustrates three different methods of calculating a tumor load for a set of discrete windows, each of which produces of a count of reads in a discrete window, which may be combined to determine a tumor load score, in accordance with some embodiments.

FIG. 3 illustrates three different methods of calculating a tumor load for a set of discrete windows, each of which produces of a count of reads in a discrete window, which may be combined to determine a tumor load score, in accordance with some embodiments. In particular, FIG. 3 illustrates a first method of generating a tumor load using non-overlapping chromosomal windows ("W"), a second method of generating a tumor load using non-overlapping repeat sequence windows (e.g., non-overlapping repetitive element windows) which may comprise SINEs, LINEs, and/or low copy repeats ("SLR"), and a third method of generating a tumor load using a database of repeat sequences (e.g., a database of repetitive element windows). Any combination of the first, second, and third tumor loads may be generated using one or more of these methods. A tumor load score ("TLS") may be generated from a weighted summation of one or more of these tumor loads (e.g., using weights A, B, and/or C, respectively). A tumor load score may be indicative of the presence of tumor DNA among the cfDNA fragments present in plasma of a blood sample from the subject.

Figure 4:
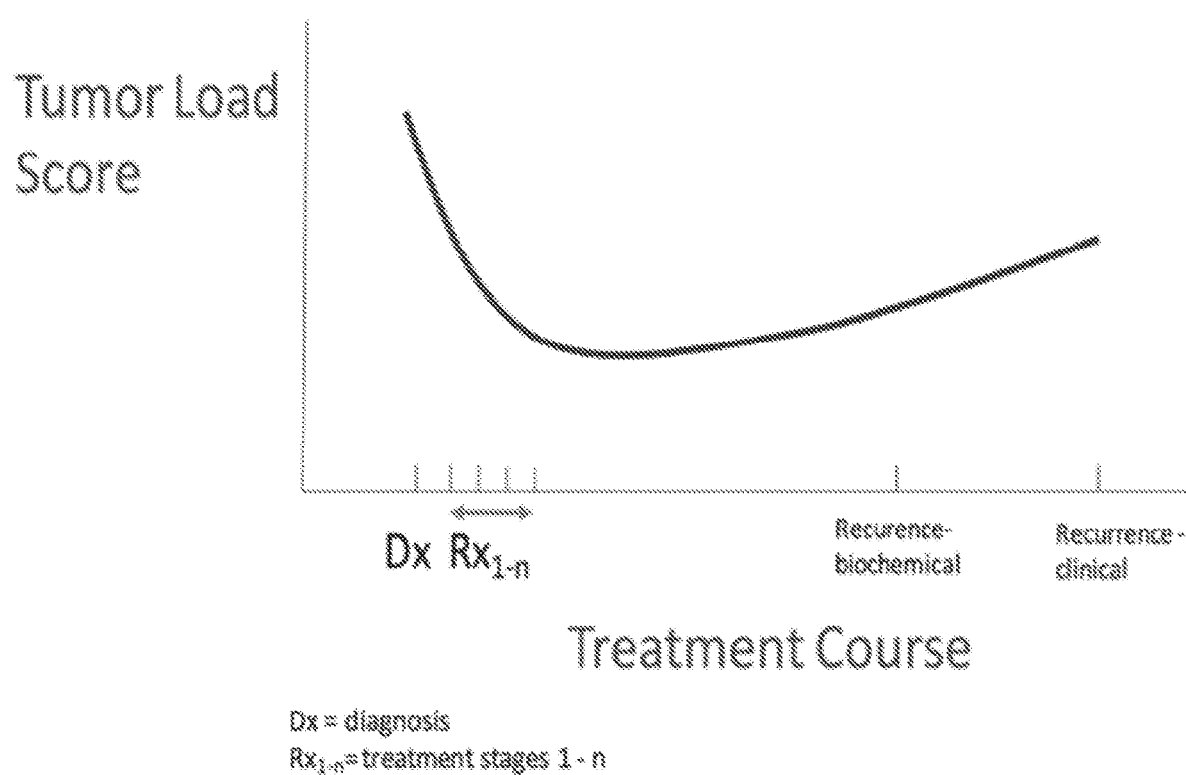
FIG. 4 illustrates change of a cancer patient's tumor load score during treatment of the patient's cancer, in accordance with some embodiments.
Figure 5:
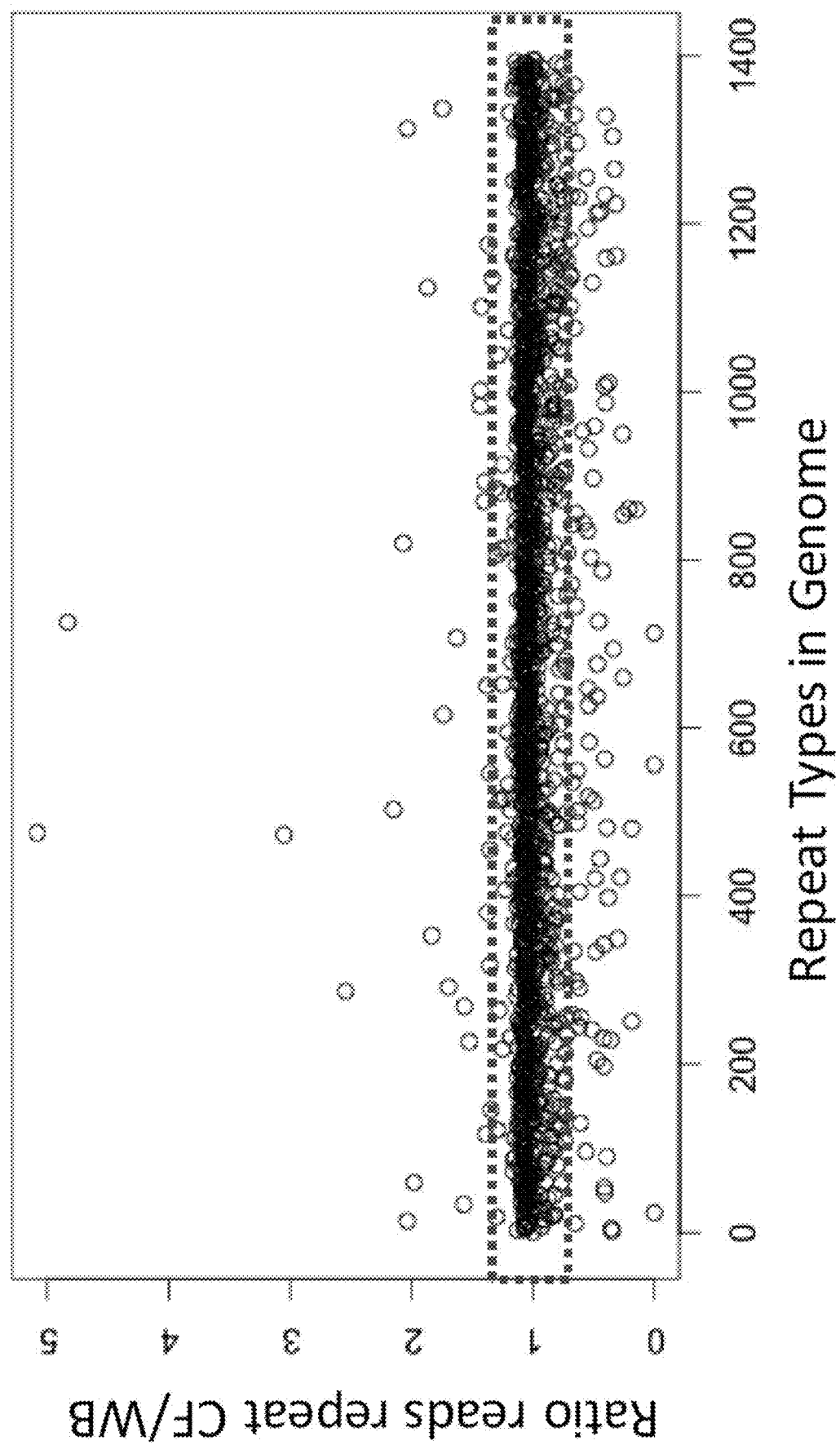
FIG. 5 illustrates a graph of ratio reads comparing a patient's cfDNA to germline DNA across a number of different repeat types, in accordance with some embodiments.

FIG. 4 illustrates change of a cancer patient's tumor load score during treatment of the patient's cancer, in accordance with some embodiments. In particular, FIG. 4 illustrates how a tumor load score varies over time as a function of the patient's treatment course. As seen in FIG. 4, a diagnosis of cancer occurs at time point 1. The patient has a particular tumor load score at the point of diagnosis. From time point 2 to time point 5, the patient is undergoing a cancer treatment, during which time duration the patient's tumor load score decreases (e.g., indicative of tumor regression and efficacy of the treatment course). After time point 5, the cancer treatment ends. After the cancer treatment has finished, the patient may receive additional assessments of the patient's tumor load score. As seen in FIG. 4, at time point 6, the patient is observed to have a residual disease or a recurrence of the cancer. In particular, the patient's recurrence of cancer may be detected and/or confirmed using various biochemical tests. Additionally, at time point 7, the patient's recurrence of cancer may be detectable by clinical methods. For example, the patient's recurrence of cancer may be detectable through the use of clinical imaging, biopsy, pathology, blood tests, cfDNA assays, etc FIG. 5 illustrates a graph of ratio reads comparing a colon cancer patient's cfDNA to germline DNA (from whole blood DNA) across a number of different repeat types, in accordance with some embodiments. In particular, FIG. 5 illustrates a graph of ratio reads (e.g., cfDNA sequencing reads ("CF") vs. whole blood DNA sequencing reads ("WB")) for a plurality of repeat types in a genome based on analysis of a sample from a patient, as assessed against a threshold used for outlier determination. In particular, ratios (e.g., CF/WB) of for a particular repeat (e.g., repetitive element) that are between 0.75 and 1.25 are interpreted as not showing a great preference for that particular repeat in the cfDNA sample versus the whole blood DNA sample of the patient (e.g., not an outlier for that repetitive element). However, ratios for a particular repeat (e.g., repetitive element) that are less than 0.75 or more than 1.25 (e.g., more than 0.25 away from a 1.0 ratio) are interpreted as showing a significant preference for that particular repeat in the cfDNA sample versus the whole blood DNA sample (e.g., CF/WB) for the patient. Other possible sets of cutoff ratio ranges may be interpreted as showing a significant presence for particular repeats in the cfDNA sample versus the germline (e.g., whole blood sample) DNA sample for the patient, such as (i) less than 0.95 or more than 1.05 (e.g., more than 0.05 away from a 1.0 ratio), (ii) less than 0.9 or more than 1.1 (e.g., more than 0.1 away from a 1.0 ratio), (iii) less than 0.85 or more than 1.15 (e.g., more than 0.15 away from a 1.0 ratio), (iv) less than 0.8 or more than 1.2 (e.g., more than 0.2 away from a 1.0 ratio), (v) less than 0.7 or more than 1.3 (e.g., more than 0.3 away from a 1.0 ratio), and (vi) less than 0.65 or more than 1.35 (e.g., more than 0.35 away from a 1.0 ratio). Different types of ratios may be calculated for this type of graph as well, such as (i) CF/BC ratios of cfDNA sequencing reads ("CF") vs. buffy coat DNA sequencing reads ("BC") and (ii) BC/WB ratios of buffy coat sequencing reads ("BC") vs. whole blood DNA sequencing reads ("WB").

Figure 6:
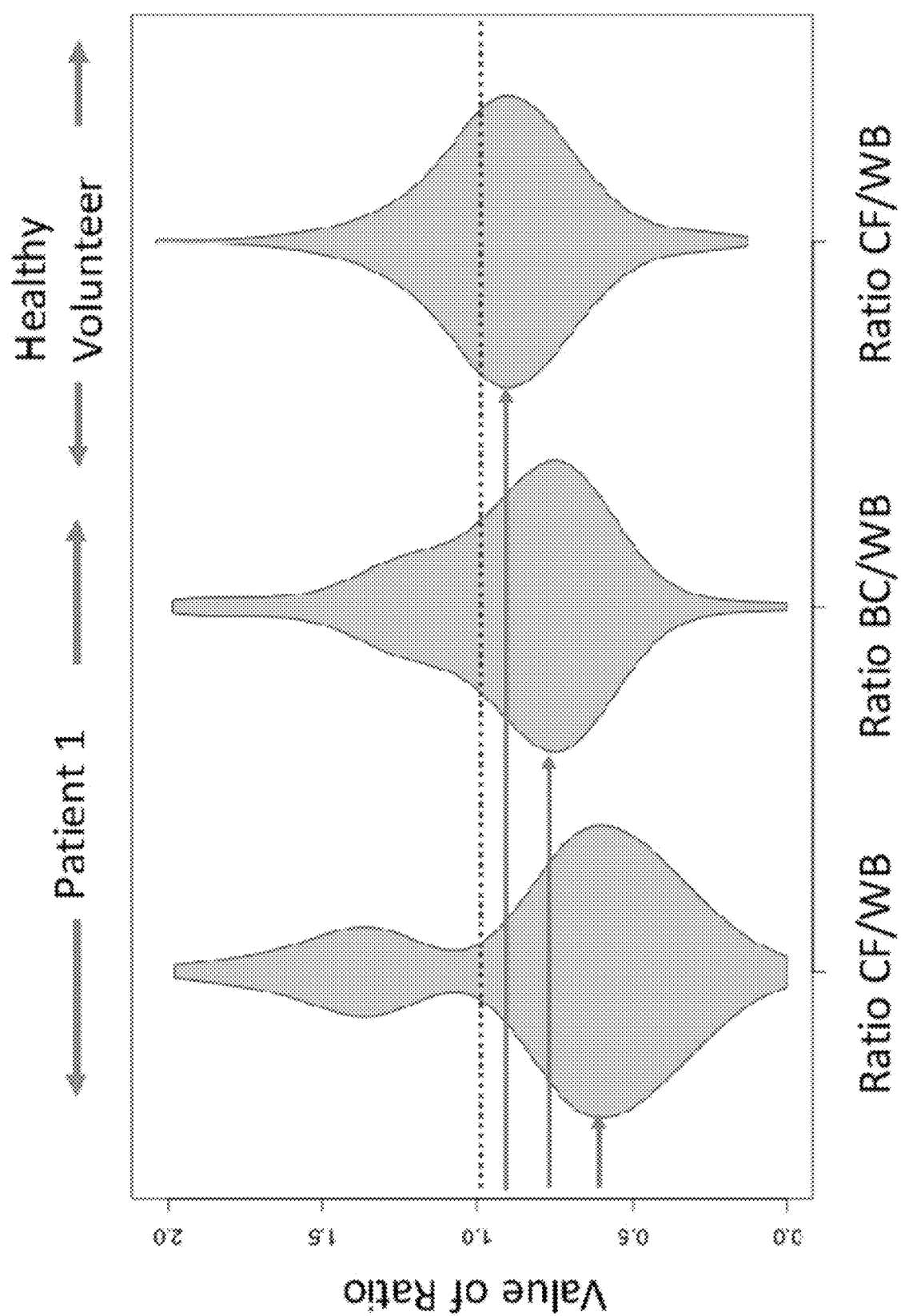
FIG. 6 illustrates graphical plots of ratios between different types of DNA sequence data of subjects, in accordance with some embodiments.

FIG. 6 illustrates graphical plots of ratios between different types of DNA sequence data of subjects. In particular, FIG. 6 illustrates a ratio of different types of DNA sequence data across 153 particular repeat sequences (repetitive elements). As seen in FIG. 6, a first graphical plot is provided that illustrates a comparison of cfDNA sequence data ("CF") and whole blood DNA sequence data ("WB") of a cancer patient. Additionally, a second graphical plot is provided that illustrates a comparison of buffy coat DNA sequence data ("BC") and whole blood DNA sequence data ("WB") of a cancer patient. Further, a third graphical plot is provided that illustrates a comparison of cfDNA sequence data ("CF") and whole blood DNA sequence data ("WB") of a healthy volunteer (e.g., a subject without cancer). As seen in FIG. 6, a shift in distribution is observed between the Ratio CF/WB versus the ratio BC/WB (solid arrows) for the cancer patient, suggesting more tumor DNA is present the cfDNA compartment. In addition, a shift in distribution is observed between the CF/WB ratios of the colon cancer patient versus the healthy volunteer. In the healthy volunteer, the frequency ratio of the repeats is closely centered around 1.0, suggesting no change in the genomes from the cfDNA versus whole blood.

Figure 7:
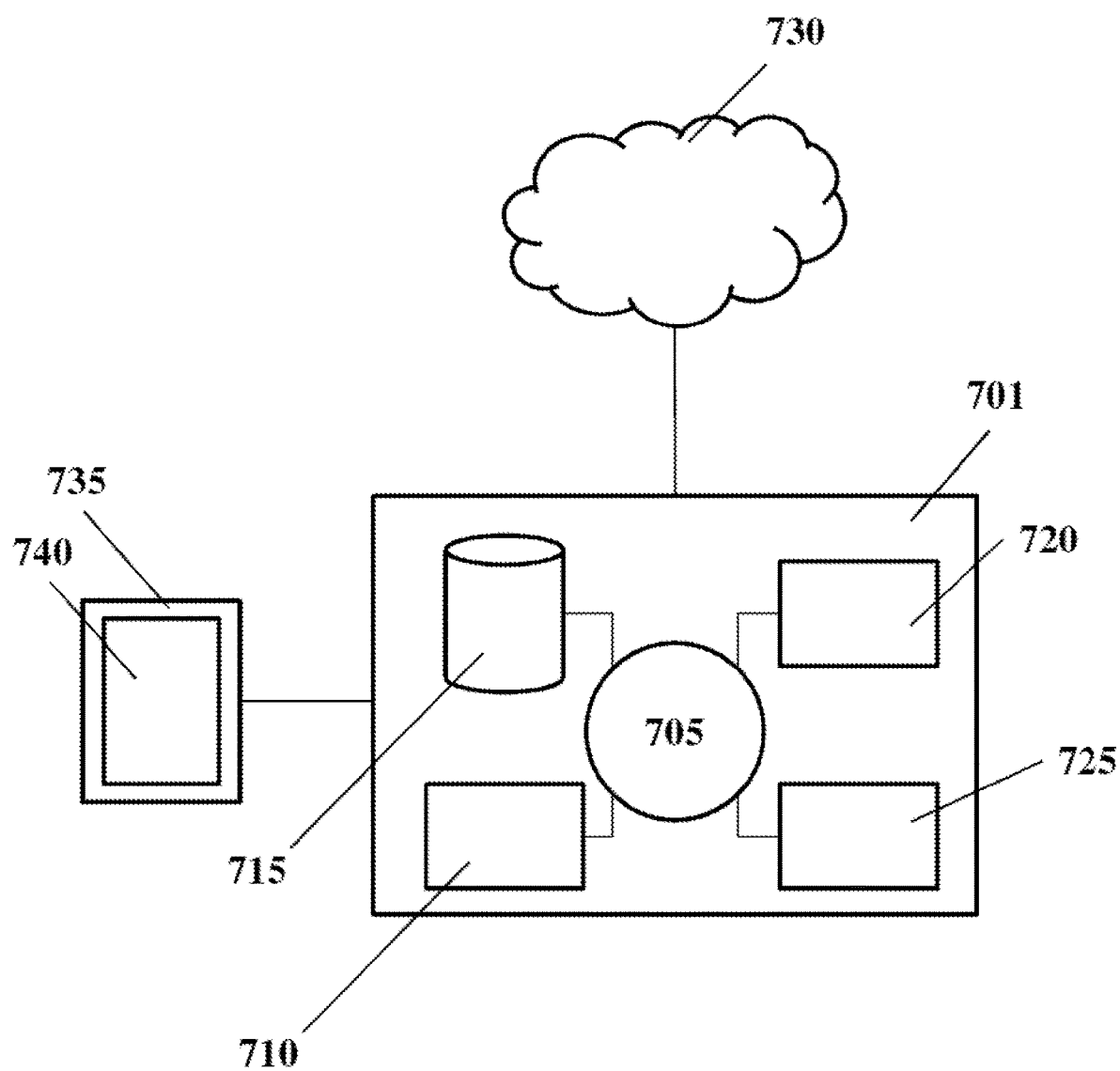
FIG. 7 illustrates a computer control system that is programmed or otherwise configured to implement methods provided herein.

FIG. 7 illustrates a computer control system that is programmed or otherwise configured to implement methods provided herein.

EXAMPLES

Example 1: Isolation of cfDNA and Germline DNA from a Sample of a Subject

In order to isolate cell-free DNA (cfDNA) and germline DNA from a subject (e.g., a patient), a single draw is made of whole blood into a 10 milliliter (mL) Streck tube (Streck Cell-Free DNA BCT Catalog #218962). The single tube is then processed as outlined in the following sections and as outlined in FIG. 1.

Whole Blood Processing for Cell-Free DNA
1. Centrifuge Streck tube containing whole blood at 1,600 g for 15 minutes (min).
2. Carefully aspirate 1 mL of the uppermost plasma layer and transfer to a 2 mL microtube (Fisher Low Retention 2 mL microtubes, Catalog #02-681-332), avoiding the buffy coat and red cell layers.
3. Repeat step 2 until all plasma is depleted.
4. Set the tube Streck Tube aside (see Whole Blood Processing for White Blood Cell Pellet below for continue processing of this sample)
5. Label each tube, ranking each aliquot from top plasma layer to bottom.
6. Centrifuge each microtube of plasma at 2,500 g for 10 min.
7. Label each tube while including its rank from the above collection.
8. Carefully aspirate 800 microliters (μL) of the uppermost plasma and transfer to a fresh 2 mL microtube. The cell pellet, along with about 200 μL of supernatant should remain. (Each Streck Tube typically yields 3 to 4 tubes worth of plasma, each containing ~800 μL. These tubes should immediately be taken through step 9 or immediately stored at −80° C.)
9. Using the single tube isolated from the topmost aliquot of the plasma fraction, follow the Q1Aamp DSP DNA Mini kit (Qiagen Catalog#61104) protocol to isolate DNA from plasma.

Whole Blood Processing for White Blood Cell Pellet
1. Carefully pipette the buffy coat (from Streck Tube previously set aside from Step 4 in Whole Blood Processing for Cell-free DNA) into a 2 mL tube.
2. Centrifuge the microtube at 400 g for 5 minutes.
3. Aspirate and discard any excess supernatant (likely plasma), leaving the pellet behind.
4. Resuspend the pellet in 1ml of Phosphate Buffered Saline (PBS).
5. Centrifuge the microtube at 400 g for 5 min.
6. Aspirate and discard any excess supernatant.
7. Follow the QIAamp DSP DNA Mini kit (Qiagen) protocol to isolate DNA from white blood cells (WBCs).

Validate cfDNA and Germline DNA Quality
1. The isolated cfDNA is BioAnalyzed to determine sizes of yielded fragments. This was run on a High Sensitivity DNA Bioanalysis chip. FIG. 2 shows an example DNA size distribution. The amount of cfDNA within healthy subjects varies; on average, the yield is 20 ng/mL of plasma. The molecular size of the resulting cfDNA isolate is generally between 170-500 base pairs (bp) with a large peak at about 170 bp. The germline DNA retains a size of >50 kilobases (kb).

Example 2: DNA Sequencing of cfDNA and Germline DNA

Sequencing libraries are created from cell-free DNA and germline DNA using standard protocols, for example, those supplied by Illumina. These libraries are quality checked using an Agilent Bioanalyzer to determine the molecular size profile needed for good quality sequencing libraries (400-600 bp). The resulting libraries are sequenced on a Illumina HiSeq 2500 flowcell to a depth of approximately 6-fold haploid genome coverage (e.g., 6×). The paired-end 100-bp reads that are created by this sequencing approach are analyzed as outlined in Examples 3-6 below.

Example 3: Detection of Tumor DNA from cfDNA Using DNA Sequencing Reads in Discrete Chromosomal Windows of a Reference Genome The sequence read data is employed from Example 2 above and the following operations are executed on these sequence reads.

All sequence reads are aligned to a database of the human genome sequence using the Burrows-Wheeler Algorithm (Li and Durbin, 2010). The output of this operation is a detailed position, in chromosomal coordinates (chromosome identifier, leftmost coordinate of a read, rightmost coordinate of a read), of each read in the genome. Also provided is whether a read is well aligned and also whether the other read in the same pair is also aligned to the genome. The alignment of read pairs provides a good indicator that each individual read alignment is correct. Finally, a list of all the reads that cannot be aligned to the genome is provided.

A plurality of non-overlapping chromosomal windows of a reference genome is defined. The chromosomal windows each have a pre-defined size of W kilobases (kb) (e.g., where W can be 1 kb, 5 kb, 10 kb, 50 kb, 100 kb, 500 kb, 1000 kb, etc.). The location of each window (as defined by the left-most and right-most positions) in the genome is identified by the location of the corresponding chromosome.

The number of reads that are aligned within each chromosomal window are counted for two sets of reads: (i) cfDNA ($R_{C\text{-}CF}$) and (ii) germline sample ($R_{C\text{-}GERMLINE}$). The location of a read can be approximated by using the single coordinate of its 5'-most location, which is the same as the lowest genomic coordinate value.

Tumor cfDNA$_W$ is calculated as the logarithm of the ratio of the cfDNA read counts found within each chromosomal window in relation to the germline read counts found within the same chromosomal window, e.g., Tumor cfDNA$_W$=log($R_{W\text{-}CF}/R_{W\text{-}GERMLINE}$). Due to the logarithm transformation, the Tumor cfDNA ratio can be greater than zero (if $R_{W\text{-}CF} > R_{W\text{-}GERMLINE}$), less than zero (if $R_{W\text{-}CF} < R_{W\text{-}GERMLINE}$), or equal to zero (if $R_{W\text{-}CF} = R_{W\text{-}GERMLINE}$).

Tumor load is calculated as a summation across a plurality of chromosomal windows in the reference genome. The plurality of chromosomal windows may comprise a subset or all possible chromosomal windows in the reference genome.

$$\text{Tumor } Load_C = \sum_{1}^{chromosomes} \text{Tumor } cfDNA_C$$

Example 4: Detection of Tumor DNA from cfDNA Using DNA Sequencing Reads in Discrete Repetitive Element Windows of a Reference Genome The sequence read data is employed from Example 2 above and all sequence reads are aligned according to Example 3 above. The following operations are executed on these sequence reads.

Using the exact genomic coordinates of Short Interspersed Elements (SINEs), Long Interspersed Elements (LINEs), and low copy repeats identified on the genome obtained from the University of California at Santa Cruz (http://genome.uscs.edu), a plurality of non-overlapping windows are defined that correspond to each repeat type with its corresponding location in the genome. This partitioned region of the genome is defined as an SLR (SINE, LINE, or low copy repeat).

The number of reads that are aligned within each repetitive element (SLR) window are counted for two sets of reads: (i) cfDNA ($R_{SLR\text{-}cfDNA}$) and (ii) germline sample ($R_{SLR\text{-}germline}$). The location of a read can be approximated to by using the single coordinate of its 5'-most location, which is the same as the lowest genomic coordinate value.

Tumor cfDNA$_{SLR}$ is calculated as the logarithm of the ratio of the cfDNA read counts found within each repetitive element window in relation to the germline read counts found within the same repetitive element window, e.g., Tumor cfDNA$_{SLR}$=log($R_{SLR\text{-}CF}/R_{SLR\text{-}GERMLINE}$). Due to the logarithm transformation, the Tumor cfDNA ratio can be greater than zero (if $R_{SLR\text{-}CF} > R_{SLR\text{-}GERMLINE}$), less than zero (if $R_{SLR\text{-}CF} < R_{SLR\text{-}GERMLINE}$), or equal to zero (if $R_{SLR\text{-}CF} = R_{SLR\text{-}GERMLINE}$).

Tumor load$_W$ is calculated as a summation across a plurality of chromosomal windows in the reference genome. The plurality of repetitive element windows may comprise a subset or all possible repetitive element windows in the reference genome.

$$\text{Tumor } Load_{SLR} = \sum_{1}^{SLR} \text{Tumor } cfDNA_{SLR}$$

Example 5: Detection of Tumor DNA from cfDNA Using DNA Sequencing Reads in a Database of Repetitive Element Windows The sequence read data are employed from Example 2 above and the following operations are executed on these sequence reads.

All sequence read pairs are aligned to a database of SINEs and LINEs (e.g., repetitive elements) using the Burrows-Wheeler-Algorithm (Li and Durbin, 2010). This database provides the sequence structure of each different repeat type and chromosomal coordinates in the human genome where these are found. The output of this operation is the specification of the read alignment in repeat region type and chromosomal coordinates (chromosome identifier, left-most coordinate of a read, and right-most coordinate of a read), of each read in the genome. Information that determines whether the particular read and its pair is aligned is less important, as long as either read of a read-pair are aligned to the SINEs and LINEs database that is sufficient. Finally, a list of all the reads that cannot be aligned to the genome is provided.

The result of this approach is a total count of the number of cfDNA reads $R_{REP\text{-}CF}$ and germline DNA reads $R_{REP\text{-}GERMLINE}$ that corresponds each repeat type structure found at a particular chromosomal coordinate.

Tumor load$_{REP}$ is calculated as the logarithm of the ratio of the cfDNA read counts for any one particular kind of repeat type constituting SINEs, LINEs, or low copy repeats to the germline read counts for the same kind of repeat type constituting SINEs, LINEs, or low copy repeats, e.g., Tumor cfDNA$_{REP}$=log($R_{REP\text{-}CF}/R_{REP\text{-}GERMLINE}$). Due to the logarithm transformation, the Tumor cfDNA ratio can be greater than zero (if $R_{REP-CF} > R_{REP-GERMLINE}$), less than zero (if $R_{REP-CF} < R_{REP-GERMLINE}$), or equal to zero (if $R_{REP-CF} = R_{REP-GERMLINE}$).

Tumor Load$_{REP}$ is calculated as a summation of the plurality of repetitive element windows from the database of repetitive element windows across all the discrete families of repeat structure.

$$\text{Tumor Load}_{REP} = \sum_{1}^{repeat\ regions} \text{Tumor } cfDNA_{REP}$$

Example 6: Generation of Tumor Load Score Using One or More Methods to Assess Tumor Load A bioinformatics process using a combination of the processes of Examples 3-5 is employed. There are up to three components to this process, each of which involves counting the number of reads from cfDNA and germline DNA fractions: (1) in non-overlapping (discrete) chromosomal windows of defined base length across the genome to generate a Tumor Load$_W$ (Example 3), (2) in non-overlapping (discrete) repetitive element (SLR) windows of defined length of the genome to generate a Tumor Load$_{SLR}$ (Example 4), and (3) that contain sequence motifs identifying them as components of repetitive elements by reference to a database of repetitive elements to generate a Tumor Load$_{REP}$ (Example 5). The methods described in Examples 4 and 5 are different, since there may be some sequencing reads that cannot be aligned to the human genome (as required in Example 4) but that may be identified as a repeat sequence containing an SLR (as enabled by Example 5). The overall method of tumor load assessment is illustrated at a high level in FIG. 3.

The combination of the overall Tumor Load Score (TLS) for a cancer patient can be determined by a model comprised of each of one, two, three, four, or more than four of the preceding Tumor Load measurements (e.g., from Examples 3, 4, or 5):

TLS=$A$*Tumor Load$_W$+$B$*Tumor Load$_{SLR}$+$C$*Tumor Load$_{REP}$+$D$

The linear model represented here with coefficient values, A, B, C, and D, can be discovered from a group of subjects (e.g., patients whose clinical measurements are indicative of either treatment response or treatment non-response, or healthy subjects). For example, the set of coefficients (A, B, C, and D) can be calculated by linear regression (e.g., linear least squares regression) on the clinical measurement data.

The TLS value can change over treatment course as outlined by the theoretical relationship in FIG. 4. The TLS, when measured consistently and frequently throughout a patient's treatment, can enable the detection of early disease recurrence as denoted by the chronological event "Recurrence—biochemical" in FIG. 4 which occurs at an earlier time point than the current standard of care event corresponding to "Recurrence—clinical".

Example 8: Generation of Tumor Load Score

The methodology of Example 4 was executed in a colon cancer patient sample using the following variation of the equation above Tumor Load$_{SLR}$. The input data for this particular example are sequence reads from the cfDNA from plasma and the germline compartments of the patient's whole blood. The whole blood genomes sequenced include those from isolated white blood cells (buffy coat—or BC) and whole blood (combination of plasma, serum and buffy coat—or WB):

1. Count the number of reads found at each chromosomal locus which is defined as a repeat sequence, as define above as SLR, in the CF, BC and WB genomes.
2. Determine the ratio of the number reads found in each repeat class defined in the genome, SLR as defined above, from the cfDNA of a patient relative to the reads in the same repeat class found in the genomes of white blood cells of the same patient. This produces 1,395 ratio values, one for each repeat class defined in the genome, the vast majority of which have a value of 1 (see FIG. 5), however in some repeats there is a skew in the repeat ratio in the cfDNA sample versus whole blood sample i.e. CF/WB>1.25 or CF/WB<0.75. These repeat ratios provide classification power for the cfDNA sample.
3. Plot the distributions of the repeat ratio of CF/WB using only the values>1.25 or <0.75. For the colon cancer patient sample exemplified here there are 153 repeat ratios that fulfill such criteria (see FIG. 6, left hand plot).
4. Plot the distribution of the same 153 repeat ratios found in Step 3, only this time for buffy coat (BC—white blood cells containing mostly germline DNA) versus whole blood (WB). This is the middle plot in FIG. 6—ratio BC/WB. This highlights the fact that there is a subset of repeat sequence types in the cfDNA compartment that have the capacity to show different frequency preferences when compared to the same repeat sequences from the buffy coat (white blood cells) which is mostly comprised of germline DNA. This signifies that the genome structure is different in the cfDNA compartment relative to the germline compartment which is indicative of tumor occurrence in the cfDNA compartment. The distribution in FIG. 6 (middle plot) for BC/WB shows a reduction in preferential occurrence of repeat types (less skew) as compared with the cfDNA based ratio. The ratio of BC/WB distribution is closer to the distribution of the same 153 repeats found in cfDNA ratio (CF/WB) from a healthy volunteer, which further suggests that the cfDNA ratio of 153 repeats from the cancer patient is driven by the presence of detectable tumor DNA.

A consequence of this scoring approach is that each patient possesses a discrete set of repeat sequence types that enable the classification of tumor DNA in the cfDNA compartment (no more than 50% of scoring repeat sequences are shared between patients). In this manner this scoring approach defines an individualized signature of tumor DNA for the patient that can be tracked during therapy.

Computer Control Systems

The present disclosure provides computer control systems that are programmed to implement methods of the disclosure. FIG. 7 shows a computer system 701 that is programmed or otherwise configured to analyze sequencing information, generate tumor load scores based on analysis of the genomic sequencing information, and generate plots of tumor load scores as a function of two or more different time points. The computer system 701 can regulate various aspects of analysis, calculation, and generation of the present disclosure, such as, for example, analysis of sequencing information, generation of tumor load scores based on analysis of the genomic sequencing information, and generation of plots of tumor load scores as a function of two or more different time points. The computer system 701 can be an electronic device of a user or a computer system that is remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., a physician, a nurse, a caretaker, a patient, or a subject). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, analysis results of sequencing information, tumor load scores generated based on analysis of the genomic sequencing information, and plots of tumor load scores generated as a function of two or more different time points. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, analyze sequencing information, generate tumor load scores based on analysis of the genomic sequencing information, and generate plots of tumor load scores as a function of two or more different time points.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for assessing a tumor load for a subject, the method comprising:
    obtaining a first sample from the subject at a first time point;
    isolating cell-free DNA (cfDNA) from the first sample;
    sequencing the isolated cfDNA to produce first cfDNA sequencing reads;
    obtaining a second sample from the subject;
    isolating germline DNA from the second sample;
    sequencing the isolated germline DNA to produce germline DNA sequencing reads;
    aligning the first cfDNA sequencing reads to a reference genome;
    aligning the germline DNA sequencing reads to the reference genome;
    generating a quantitative measure of the first cfDNA sequencing reads for each of a plurality of non-overlapping repetitive element windows of the reference genome to generate a first cfDNA set;
    generating a quantitative measure of the germline DNA sequencing reads for each of the plurality of non-overlapping repetitive element windows to generate a germline DNA set; and
    generating a first tumor load score based on a first set of ratio values, wherein the first set of ratio values comprises, for each of the plurality of non-overlapping repetitive element windows, a ratio of the quantitative measure in the first cfDNA set to the quantitative measure in the germline DNA set, and wherein the first tumor load score is indicative of the tumor load for the subject.

2. The method of claim 1, further comprising determining whether the first tumor load score is greater than a predetermined threshold, wherein a first tumor load score greater than the predetermined threshold indicates a presence of a cancer in the subject.

3. The method of claim 1, further comprising:
    obtaining a third sample from the subject at a second time point;
    isolating cell-free DNA (cfDNA) from the third sample;
    sequencing the cfDNA isolated from the third sample to produce second cfDNA sequencing reads;
    aligning the second cfDNA sequencing reads to the reference genome;
    generating a quantitative measure of the second cfDNA sequencing reads for each of the plurality of non-overlapping repetitive element windows to generate a second cfDNA set; and
    generating a second tumor load score based on a second set of ratio values, wherein the second set of ratio values comprises, for each of the plurality of non-overlapping repetitive element windows, a ratio of the quantitative measure in the second cfDNA set to the quantitative measure in the germline DNA set.

4. The method of claim 3, further comprising determining a difference between the first tumor load score and the second tumor load score, wherein the difference is indicative of a progression or regression of a tumor of the subject.

5. The method of claim 3, further comprising generating a plot of the first tumor load score and the second tumor load score as a function of the first time point and the second time point, wherein the plot is indicative of the progression or regression of the tumor of the subject.

6. The method of claim 3, further comprising, after isolating the cfDNA from the third sample and prior to sequencing the cfDNA isolated from the third sample: generating a third library from the cfDNA isolated from the third sample, wherein sequencing the cfDNA isolated from the third sample to produce the second cfDNA sequencing reads comprises sequencing the third library.

7. The method of claim 1, wherein the plurality of non-overlapping repetitive element windows comprises a plurality of non-overlapping windows associated with repetitive elements selected from the group consisting of Short Interspersed Elements (SINEs), Long Interspersed Elements (LINEs), and low copy repeats.

8. The method of claim 1, wherein the first sample and/or the second sample are blood samples.

9. The method of claim 1, wherein the first and the second samples are the same sample, and wherein the germline DNA comprises buffy coat DNA and/or whole blood DNA.

10. The method of claim 1, wherein the first and the second samples are different samples obtained from the subject at the first time point.

11. The method of claim 1, wherein the first and the second samples are different samples obtained from the subject at different time points.

12. The method of claim 1, further comprising, after isolating the cfDNA from the first sample and prior to sequencing the isolated cfDNA: generating a first library from the isolated cfDNA, wherein sequencing the isolated cfDNA to produce the first cfDNA sequencing reads comprises sequencing the first library.

13. The method of claim 1, further comprising, after isolating the germline DNA from the second sample and prior to sequencing the isolated germline DNA: generating a second library from the isolated germline DNA, wherein sequencing the isolated germline DNA to produce the germline DNA sequencing reads comprises sequencing the second library.

14. A computer-implemented method for assessing a tumor load for a subject, the method comprising:
  obtaining a first sample from the subject at a first time point;
  isolating cell-free DNA (cfDNA) from the first sample;
  sequencing the isolated cfDNA to produce first cfDNA sequencing reads;
  obtaining a second sample from the subject;
  isolating germline DNA from the second sample;
  sequencing the isolated germline DNA to produce germline DNA sequencing reads;
  aligning the first cfDNA sequencing reads to a plurality of repetitive element windows from a database of repetitive element windows;
  aligning the germline DNA sequencing reads to the plurality of repetitive element windows;
  generating a quantitative measure of the first cfDNA sequencing reads for each of the plurality of repetitive element windows to generate a first cfDNA set;
  generating a quantitative measure of the germline DNA sequencing reads for each of the plurality of repetitive element windows to generate a germline DNA set; and
  generating a first tumor load score based on a first set of ratio values, wherein the first set of ratio values comprises, for each of the plurality of repetitive element windows, a ratio of the quantitative measure in the first cfDNA set to the quantitative measure in the germline DNA set, and wherein the tumor load score is indicative of the tumor load for the subject.

15. The method of claim 14, further comprising determining whether the first tumor load score is greater than a predetermined threshold, wherein a first tumor load score greater than the predetermined threshold indicates a presence of a cancer in the subject.

16. The method of claim 14, further comprising:
  obtaining a third sample from the subject at a second time point;
  isolating cell-free DNA (cfDNA) from the third sample;
  sequencing the cfDNA isolated from the third sample to produce second cfDNA sequencing reads;
  aligning the second cfDNA sequencing reads to the plurality of repetitive element windows;
  generating a quantitative measure of the second cfDNA sequencing reads for each of the plurality of repetitive element windows to generate a second cfDNA set; and
  generating a second tumor load score based on a second set of ratio values, wherein the second set of ratio values comprises, for each of the plurality of repetitive element windows, a ratio of the quantitative measure in the second cfDNA set to the quantitative measure in the germline DNA set.

17. The method of claim 16, further comprising determining a difference between the first tumor load score and the second tumor load score, wherein the difference is indicative of a progression or regression of a tumor of the subject.

18. The method of claim 16, further comprising generating a plot of the first tumor load score and the second tumor load score as a function of the first time point and the second time point, wherein the plot is indicative of the progression or regression of the tumor of the subject.

19. The method of claim 16, further comprising, after isolating the cfDNA from the third sample and prior to sequencing the cfDNA isolated from the third sample: generating a third library from the cfDNA isolated from the third sample, wherein sequencing the cfDNA isolated from the third sample to produce the second cfDNA sequencing reads comprises sequencing the third library.

20. The method of claim 14, wherein the database of repetitive element windows comprises a plurality of windows associated with repetitive elements selected from the group consisting of Short Interspersed Elements (SINEs), Long Interspersed Elements (LINEs), and low copy repeats.

21. The method of claim 14, wherein the first sample and/or the second sample are blood samples.

22. The method of claim 14, wherein the first and the second samples are the same sample, and wherein the germline DNA comprises buffy coat DNA and/or whole blood DNA.

23. The method of claim 14, wherein the first and the second samples are different samples obtained from the subject at the first time point.

24. The method of claim 14, wherein the first and the second samples are different samples obtained from the subject at different time points.

25. The method of claim 14, further comprising, after isolating the cfDNA from the first sample and prior to sequencing the isolated cfDNA: generating a first library from the isolated cfDNA, wherein sequencing the isolated cfDNA to produce the first cfDNA sequencing reads comprises sequencing the first library.

26. The method of claim 14, further comprising, after isolating the germline DNA from the second sample and prior to sequencing the isolated germline DNA: generating a second library from the isolated germline DNA, wherein sequencing the isolated germline DNA to produce the germline DNA sequencing reads comprises sequencing the second library.

27. The method of claim 1 or 14, wherein the germline DNA comprises buffy coat DNA or whole blood DNA.

28. The method of claim 1 or 14, wherein the quantitative measures of the cfDNA sequencing reads and the germline DNA sequencing reads are counts of DNA sequencing reads that are aligned with a given window.

29. The method of claim 1 or 14, wherein generating the first tumor load score based on the first set of ratio values comprises (i) performing a logarithm transformation of the first set of ratio values to generate a first set of log ratio values and (ii) performing a summation of the first set of log ratio values, and wherein generating the second tumor load score based on the second set of ratio values comprises (iii) performing a logarithm transformation of the second set of ratio values to generate a second set of log ratio values and (iv) performing a summation of the second set of log ratio values.

* * * * *